United States Patent
Jacobson et al.

(10) Patent No.: US 10,016,432 B2
(45) Date of Patent: Jul. 10, 2018

(54) METHANOCARBA DERIVATIVES OF PSEUDORIBOSE THAT INHIBIT ADENOSINE KINASE

(71) Applicants: Legacy Emanuel Hospital & Health Center, Portland, OR (US); The United States of America, as represented by the Secretary, Department of Health and Human Services, Washington, DC (US)

(72) Inventors: Kenneth Alan Jacobson, Silver Spring, MD (US); Detlev Boison, Portland, OR (US); Kiran Shambhu Toti, Rockville, MD (US)

(73) Assignees: Legacy Emanuel Hospital & Health Center, Portland, OR (US); The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

(21) Appl. No.: 15/607,379

(22) Filed: May 26, 2017

(65) Prior Publication Data
US 2017/0340640 A1    Nov. 30, 2017

Related U.S. Application Data

(60) Provisional application No. 62/342,854, filed on May 27, 2016.

(51) Int. Cl.
C07D 487/04 (2006.01)
A61K 31/519 (2006.01)

(52) U.S. Cl.
CPC .......... *A61K 31/519* (2013.01); *C07D 487/04* (2013.01)

(58) Field of Classification Search
CPC ............................ C07D 487/04; A61K 31/519
USPC ...................... 544/280; 536/26.7; 514/258.1
See application file for complete search history.

(56) References Cited

U.S. PATENT DOCUMENTS

| | | | |
|---|---|---|---|
| 6,030,969 A | 2/2000 | Bhagwat et al. | |
| 8,518,957 B2 | 8/2013 | Jacobson et al. | |
| 2003/0216412 A1 | 11/2003 | Jacobson et al. | |
| 2006/0270629 A1 | 11/2006 | Jacobson et al. | |
| 2011/0046166 A1 | 2/2011 | Jacobson et al. | |
| 2012/0184569 A1 | 7/2012 | Jacobson et al. | |
| 2013/0338173 A1 | 12/2013 | Olhava et al. | |

FOREIGN PATENT DOCUMENTS

WO    9846603 A1    10/1998
WO    2006091905 A1    8/2006

OTHER PUBLICATIONS

Jacobson et al., "Methanocarba Analogues of Purine Nucleosides as Potent and Selective Adenosine Receptor Agonists", J. Med. Chem., 2000, 43 (11), pp. 2196-2203.
McGaraughty et al. "Recent Developments in the Discovery of Novel Adenosine Kinase Inhibitors: Mechanism of Action and Therapeutic Potential", CNS Drug Reviews, 2001, vol. 7, No. 4, pp. 415-432.
Jarvis et al. "Analgesic and anti-inflammatory effects of A-286501, a novel orally active adenosine kinase inhibitor", Pain, 2002, vol. 96, pp. 107-118.
Bookser et al. "Adenosine Kinase Inhibitors. 4. 6, 8-Disubstituted Purine Nucleoside Derivatives. Synthesis, Conformation, and Enzyme Inhibition", J. Med. Chem., 2005, vol. 48, No. 9, pp. 3389-3399.
Joshi et al., "A New Synthetic Route to (North)-Methanocarba Nucleosides Designed as A3 Adenosine Receptor Agonists", J. Org. Chem., 2005, 70(2), pp. 439-447.
Maderia et al., "Biophysical studies of DNA modified with conformationally constrained nucleotides: comparison of 2'-exo (north) and 3'-exo (south) 'locked' templates", Nucleic Acids Research, 2007, 35(6), 1978-1991.
Marquez, Victor E., The Properties of Locked Methanocarba Nucleosides in Biochemistry, Biotechnology, and Medicinal Chemistry, in Modified Nucleosides: in Biochemistry, Biotechnology and Medicine, Part III Medicinal Chemistry, 2008, Chapter 12, pp. 307-341.
Melman et al., "Synthesis of Enantiomerically Pure (S)-Methanocarbaribo Uracil Nucleoside Derivatives for Use as Antiviral Agents and P2Y Receptor Ligands", J. Org. Chem., 2008, 73 (20), pp. 8085-8088.

(Continued)

*Primary Examiner* — Venkataraman Balasubramanian
(74) *Attorney, Agent, or Firm* — Kolisch Hartwell, P.C.

(57) ABSTRACT

Adenosine kinase inhibitors, including pharmaceutical compositions containing the adenosine kinase inhibitors, and their use for preventing epilepsy and its progression in patients. The adenosine kinase inhibitors have the formula:

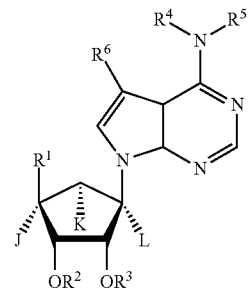

where the moieties J and K, considered in combination, are —$CH_2$—, or K and L, considered in combination, are —$CH_2$—. The $R^1$ moiety can be —$NH_2$, $C_1$-$C_6$ alkyl, $C_1$-$C_6$ alkoxy, or $C_1$-$C_6$ hydroxyalkyl. The $R^2$ and $R^3$ moieties are each independently $C_1$-$C_6$ alkyl. The $R^4$ moiety is hydrogen or $C_1$-$C_6$ alkyl. The $R^5$ and $R^6$ moieties are each independently $C_6$-$C_{12}$ aryl, $C_3$-$C_8$ cycloalkyl, or $C_3$-$C_8$ heteroaryl, that is optionally further substituted.

21 Claims, 12 Drawing Sheets

(56) References Cited

OTHER PUBLICATIONS

Saneyoshi et al., "Conformationally rigid nucleoside probes help understand the role of sugar pucker and nucleobase orientation in the thrombin-binding aptamer", Nucleic Acids Research (2009), 37(17), 5589-5601.
Ludek et al., "Synthesis and Conformational Analysis of Locked Carbocyclic Analogues of 1,3-Diazepinone Riboside, a High-Affinity Cytidine Deaminase Inhibitor", J. Org. Chem., 2009, 74 (16), pp. 6212-6223.
Maruoka et al., "Pyrimidine Ribonucleotides with Enhanced Selectivity as P2Y6 Receptor Agonists: Novel 4-Alkyloxyimino, (S)-Methanocarba, and 5'-Triphosphate γ-Ester Modifications", J. Med. Chem., 2010, 53 (11), pp. 4488-4501.
Elhalem et al., "Synthesis and biological evaluation of N-thia-carba-thymidine as an antiherpetic agent", Tetrahedron (2010), 66(18), 3332-3340.
Damaraju et al., "Influence of Sugar Ring Conformation on the Transportability of Nucleosides by Human Nucleoside Transporters", ChemBioChem, 2011, vol. 12, pp. 2774-2778.
Tosh et al., "Methanocarba ring as a ribose modification in ligands of G protein-coupled purine and pyrimidine receptors: synthetic approvaches", The Royal Society of Chemistry, Med. Chem. Comm. 2013, vol. 4, pp. 619-630.
Tosh et al., "In Vivo Phenotypic Screening for Treating Chronic Neuropathic Pain: Modification of C2-Arylethynyl Group of Conformationally Constrained A3 Adenosine Receptor Agonists", J. Med. Chem., 2014, 57 (23), pp. 9901-9914.
Nayak et al., "Synthesis and Anti-Renal Fibrosis Activity of Conformationally Locked Truncated 2-Hexynyl-N6-Substituted-(N)-Methanocarba-nucleosides as A3 Adenosine Receptor Antagonists and Partial Agonists", American Chemical Society, J. Med. Chem., 2014, 57 (4), pp. 1344-1354.
Toti et al., "South (S)- and North (N)-Methanocarba-7-Deazaadenosine Analogues as Inhibitors of Human Adenosine Kinase", American Chemical Society, J. Med. Chem., 2016, 59 (14), pp. 6860-6877.
Toti et al., "Pyrimidine nucleotides containing a (5)-methanocarba ring as P2Y6 receptor agonists", The Royal Society of Chemistry, Med. Chem. Comm., 2017, vol. 8, pp. 1897-1908.
Pryde et al. "Practical synthetic routes to carbon-substituted nucleosides", Tetrahedron Letters, Sep. 24, 2011, vol. 52, pp. 6415-6419.
The U.S. Receiving Office of WIPO, International Search Report and Written Opinion of the International Searching Authority regarding PCT Patent Application No. PCT/US2017/034865 dated Sep. 8, 2017, 18 pages.
Lee et al., "Stereoselective Synthesis of 2'-C-Methyl-cydopropyl-Fused Carbanucleosides as Potential Anti-HCV Agents", Organic Letters, 2006, 8(22), 5081-5083.
Marquez et al., "The history of N-methanocarbathymidine: The investigation of a conformational concept leads to the discovery of a potent and selective nucleoside antiviral agent", Antiviral Research (2006), 71(2-3), 268-275.
Comin et al., "Sculpting the Bicyclo[3.1.0]hexane Template of Carbocydic Nucleosides to Improve Recognition by Herpes Thymidine Kinase", J. Am. Chem. Soc., 2007, 129 (19), pp. 6216-6222.
Smee et al., "Efficacy of N-methanocarbathymkfine in treating mice infected intranasally with the IHD and WR strains of vaccinia virus", Antiviral Research (2007), 76(2), 124-129.
Ludek et al., "Convergent or Linear? A Challenging Question in Carbocydic Nudeoside Chemistry", Synthesis (2007), (22), 3451-3460.
Ketkar et al., "A Nucleotide-Analogue-Induced Gain of Function Corrects the Error-Prone Nature of Human DNA Polymerase iota", J. Am. Chem. Soc., 2012, 134 (25), pp. 10698-10705.
Ketkar et al.,"Differential Furanose Selection in the Active Sites of Archaeal DNA Polymerases Probed by Fixed-Conformation Nucleotide Analogues", Biochemistry (2012), 51(45), 9234-9244.
Pallan et al., "The Conformationally Constrained N-Methanocarba-dT Analogue Adopts an Unexpected C4'-exo Sugar Pucker in the Structure of a DNA Hairpin", Biochemistry, 2012, 51 (13), pp. 2639-2641.
Guerra et al., "Synthetic Survey and Activity of 2'-deoxy-methanocarba Nucleosides", Current Organic Synthesis (2013), 10(2), 210-240.

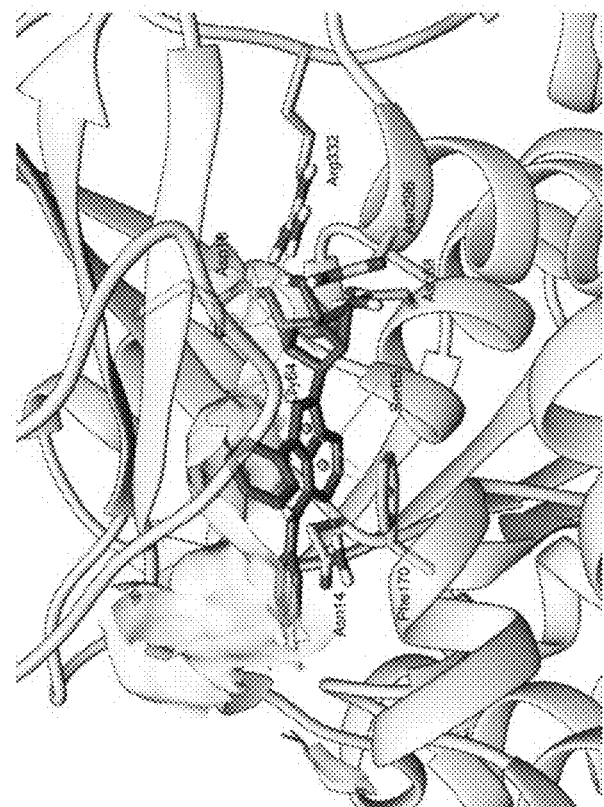
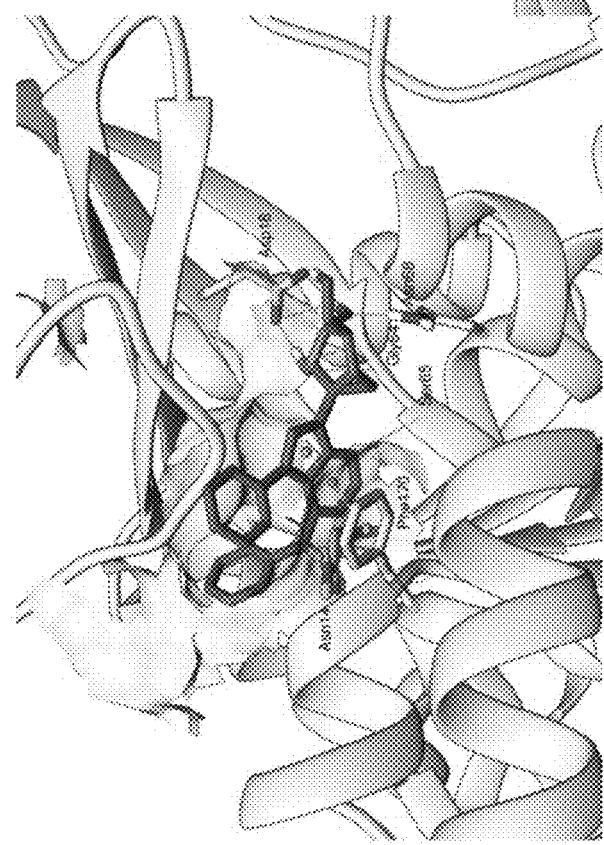
Fig. 8A
Fig. 8B

METHANOCARBA DERIVATIVES OF PSEUDORIBOSE THAT INHIBIT ADENOSINE KINASE

CROSS-REFERENCE TO PRIORITY APPLICATION

This application is based upon and claims the benefit under 35 U.S.C. § 119(e) of U.S. Provisional Patent Application Ser. No. 62/342,854, filed May 27, 2016, which is incorporated herein by reference in its entirety for all purposes.

FEDERALLY SPONSORED RESEARCH AND DEVELOPMENT

One or more inventions disclosed herein was made with Government support under NIDDK Intramural Research Program, Contract No. ZIA DK031117. The Government has certain rights in said invention or inventions.

TECHNICAL FIELD

The present disclosure relates to a novel family of adenosine kinase inhibitors, and more particularly to the prevention of epilepsy and its progression using the novel adenosine kinase inhibitors.

BACKGROUND

Endogenous adenosine (i.e., naturally occurring adenosine) acts on G protein-coupled receptors (adenosine receptors, ARs) in the central nervous system to suppress seizures and pain, and to blunt the effects of ischemia (a restriction in blood supply to tissues). In addition, adenosine has AR-independent epigenetic effects based on interactions with the transmethylation pathway. There is a dynamic equilibrium between extracellular adenosine levels and its intracellular content that is mediated by either equilibrative (ENTs) or concentrative (CNTs) transporters of nucleosides. Within the brain the concentration of adenosine is largely under the control of metabolic clearance through astrocytic adenosine kinase (AdK), which converts adenosine to 5'-AMP. By inhibiting AdK, the adenosine concentration can be exogenously raised.

It may therefore be possible to target the AR-independent effects of adenosine while avoiding excessive AR activation, by administering brain-penetrant human (h) AdK inhibitors.

SUMMARY

The present disclosure is directed to adenosine kinase inhibitors having the formula

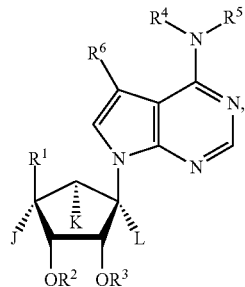

where J and K, considered in combination, are —CH$_2$—, or K and L, considered in combination, are —CH$_2$—; R$^1$ is C$_1$-C$_6$ alkyl, C$_1$-C$_6$ alkoxy, or C$_1$-C$_6$ hydroxyalkyl; R$^2$ and R$^3$ are independently C$_1$-C$_6$ alkyl; R$^4$ is hydrogen, or C$_1$-C$_6$ alkyl; and R$^5$ and R$^6$ are independently C$_6$-C$_{12}$ aryl, C$_3$-C$_8$ cycloalkyl, or C$_3$-C$_8$ heteroaryl, that is optionally further substituted.

In another aspect, the disclosure is directed to pharmaceutical compositions that include an adenosine kinase inhibitor having the formula

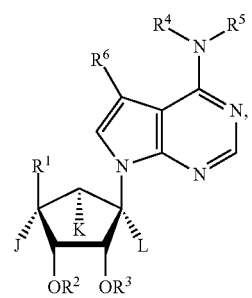

where J and K, considered in combination, are —CH$_2$—, or K and L, considered in combination, are —CH$_2$—; R$^1$ is C$_1$-C$_6$ alkyl, C$_1$-C$_6$ alkoxy, or C$_1$-C$_6$ hydroxyalkyl; R$^2$ and R$^3$ are independently C$_1$-C$_6$ alkyl; R$^4$ is hydrogen, or C$_1$-C$_6$ alkyl; and R$^5$ and R$^6$ are independently C$_6$-C$_{12}$ aryl, C$_3$-C$_8$ cycloalkyl, or C$_3$-C$_8$ heteroaryl, that is optionally further substituted.

In yet another aspect, the disclosure is directed to a method of preventing epilepsy and its progression in a patient that includes administering an effective amount of an adenosine kinase inhibitor having the formula:

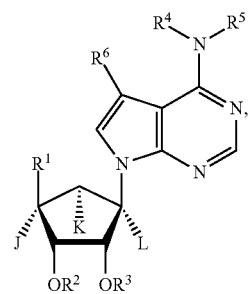

where J and K, considered in combination, are —CH$_2$—, or K and L, considered in combination, are —CH$_2$—; R$^1$ is C$_1$-C$_6$ alkyl, C$_1$-C$_6$ alkoxy, or C$_1$-C$_6$ hydroxyalkyl; R$^2$ and R$^3$ are independently C$_1$-C$_6$ alkyl; R$^4$ is hydrogen, or C$_1$-C$_6$ alkyl; and R$^5$ and R$^6$ are independently C$_6$-C$_{12}$ aryl, C$_3$-C$_8$ cycloalkyl, or C$_3$-C$_8$ heteroaryl, that is optionally further substituted.

BRIEF DESCRIPTION OF THE DRAWINGS

FIGS. 8A-8B: Docking poses of the selected methanocarba derivatives 34 (FIG. 8A) and 55 (FIG. 8B) in complex with the closed form of hAdK (PDB ID: 2I6A) obtained after IFD. Ligand and side chains of residues important for ligand recognition are reported as sticks (magenta and light blue carbon atoms, respectively). Side chains of residues establishing either van der Waals or hydrophobic contacts with the ligand are rendered as transparent surface. H-bonds are pictured as green solid lines, whereas π-π stacking interactions as cyan dashed lines with the centroids of the aromatic rings displayed as cyan spheres. Nonpolar hydrogen atoms are omitted.

DETAILED DESCRIPTION

A raised level of adenosine in the brain counteracts seizures by activating the neuroprotective A1AR and attenuates epilepsy progression by decreasing S-adenosyl methionine dependent DNA methylation as an epigenetic mechanism of action. Increased DNA methylation is a pathological hallmark of chronic epilepsy and associated with disease progression and maintenance of the epileptic state. Efficient transmethylation reactions, for example in the liver, require the removal of adenosine by AdK, and this effect has been demonstrated to occur in the brain, as well. Unlike adenosine itself, synthetic A1AR agonists, which are also proposed for seizure treatment, would not inhibit DNA methylation. Overexpression of AdK in the brain is both a result of astroglial activation and a contributing factor to epileptic seizures.

Without wishing to be bound by theory, it is believed that an inhibitor of AdK might provide an advantage in seizure control, because it would combine a pharmacological mechanism (increased A1AR activation) with epigenetic mechanisms (decreased DNA methylation) and might preferentially act on pathologically increased AdK as opposed to normal baseline levels of the enzyme. The advantages of 'adenosine augmentation therapies' for epilepsy and its associated comorbidities have already been discussed.

Figure 1:
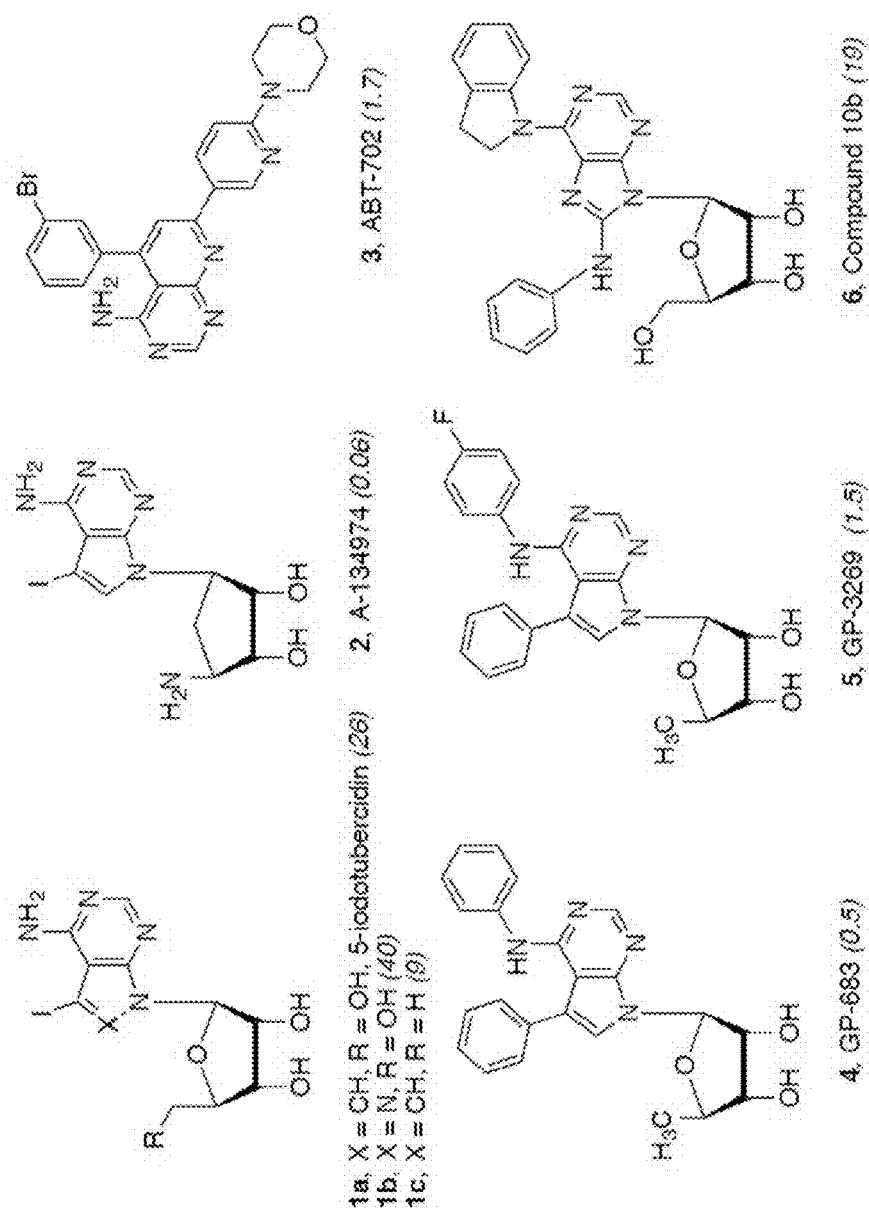
FIG. 1: A chart of nucleoside and nonnucleoside inhibitors of hAdK that have been examined in models of pain and/or seizures. Published potencies (IC50 values) for inhibition of the hAdK catalysis of the conversion of adenosine to AMP are given parenthetically in nM.

Several classes of AdK inhibitors have already been introduced and explored for the treatment of seizures and pain (see FIG. 1). One class consists of nucleosides derived from the known AdK inhibitor 7-iodo-7-deazaadenosine 1a, otherwise known as 5-iodotubercidin (5-IT). N$^7$-[(1'R,2'S, 3'R,4'S)-2',3'-Dihydroxy-4'-aminocyclopentyl]-4-amino-5-iodopyrrolopyrimidine (2, A-134974) acts in the spinal cord to reduce carrageenin-induced inflammatory hyperalgesia. Both 1a and its potent analogue, e.g. the AdK inhibitor 4-(Nphenylamino)-5-phenyl-7-(5'-deoxyribofuranosyl)pyrrolo[2,3-d]pyrimidine 4, inhibited maximal electroshock (MES) seizures in rats. Compound 4 also reduced the volumes of infarction in a model of focal cerebral ischemia in rats. Another class of nonnucleoside, heterocyclic inhibitors includes the widely used AdK inhibitor 4-amino-5-(3-bromophenyl)-7-(6-morpholino-pyridin-3-yl)pyrido[2,3-d] pyrimidine (3, ABT-702). Potent and selective inhibitors of the AdK of *Mycobacterium tuberculosis* that do not affect human AdK were found to have antimicrobial activity. AdK inhibitors were being considered for clinical trials for pain and seizure treatment in the early 2000's, but this effort was discontinued, with one of the inhibitors causing brain hemorrhage in dogs. Thus, AdK inhibition holds interest for the control of infectious, as well as neurological diseases. AdK inhibitors also induce anti-inflammatory effects that are adenosine-dependent. A potent AdK inhibitor, 4-amino-3-iodo-1-β-D-ribofuranosylpyrazolo[3,4-d]pyrimidine 1b, was also shown to indirectly reduce the expression of inducible nitric oxide synthase and tumor necrosis factor (TNF) in glial cells via activation by adenosine of Gs-coupled ARs. Recently, the AdK inhibitor 3 was found to promote rodent and porcine islet β-cell replication, which suggests the possible application of such inhibitors to the treatment of diabetes. However, other, undesired effects of the inhibitor 1a have been noted; it seems to inhibit acetyl-CoA carboxylase to promote oxidation of hepatic fatty acids and reduce de novo synthesis of lipids and cholesterol, which raises the AMP/ATP ratio. Thus, there might be a need to increase selectivity for AdK within this nucleoside series.

A common approach in medicinal chemistry to enhance the activity or selectivity of flexible biologically active, small molecules is to introduce a conformational constraint to achieve a desired conformation for interacting with a target biopolymer, i.e. here an enzyme. This may lower the energy barrier of the binding process and can eliminate undesired interactions with other molecular targets that prefer a different conformation of the ligand. One means of sterically constraining the ribose ring of nucleoside derivatives, as already applied to antiviral agents and to receptor ligands, is to incorporate a bicyclic ribose substitute in a conformation that is preferred when the molecule is bound to the protein target. The methanocarba([3.1.0]bicyclo-hexane) ring system is applied to hold the ribose-like ring in either a North (N) or a South (S) conformation. The X-ray structure of human AdK shows a bound nucleoside inhibitor 1c containing a ribose in the (S) conformation, which is similar to the ribose conformation preferred by other nucleoside kinases. The present disclosure is directed to selected sterically constraining nucleoside inhibitors of human AdK using methanocarba rings.

In one aspect, the disclosure is directed to adenosine kinase inhibitors having the formula:

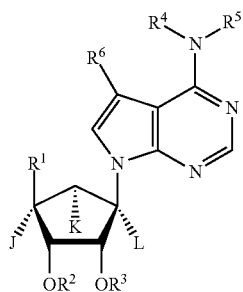

where $R^1$ is —$NH_2$, $C_1$-$C_6$ alkyl, $C_1$-$C_6$ alkoxy, or $C_1$-$C_6$ hydroxyalkyl. The substituents $R^2$ and $R^3$ are independently $C_1$-$C_6$ alkyl. The substituent $R^4$ is hydrogen, or $C_1$-$C_6$ alkyl.

The $R^5$ and $R^6$ moieties are independently selected from $C_6$-$C_{12}$ aryl, $C_3$-$C_8$ cycloalkyl, and $C_3$-$C_8$ heteroaryl. The $R^5$ and $R^6$ moieties are optionally and independently further substituted.

Where $R^5$ or $R^6$ is an aryl substituent, the aryl substituent is optionally further substituted one or more times by a halogen, a $C_1$-$C_6$ haloalkyl, a $C_1$-$C_6$ hydroxyalkyl, a $C_1$-$C_6$ alkoxy, a sulfonyloxy, carboxyalkyl, a nitro, a $C_1$-$C_6$ sulfonyloxyalkyl, or arylcarbonyl, and any combination thereof.

Where $R^5$ or $R^6$ is a cycloalkyl, the cycloalkyl substituent is optionally further substituted one or more times by a halogen, a $C_1$-$C_6$ haloalkyl, a $C_1$-$C_6$ hydroxyalkyl, a $C_1$-$C_6$ alkoxy, a sulfonyloxy, carboxyalkyl, a $C_1$-$C_6$ sulfonyloxyalkyl, or arylcarbonyl, and any combination thereof.

Where $R^5$ or $R^6$ is a heteroaryl substituent, the heteroaryl substituent is optionally further substituted one or more times by a halogen, a $C_1$-$C_6$ haloalkyl, an amino, a nitro, a $C_1$-$C_6$ alkyl, a $C_1$-$C_6$ hydroxyalkyl, a $C_1$-$C_6$ alkoxy, aryl, hydroxyl, carboxyl, sulfonyloxy, carboxyalkyl, a $C_1$-$C_6$ sulfonyloxyalkyl, a sulfonamide, a $C_1$-$C_6$ alkylcarbonyl, an arylcarbonyl, and any combination thereof.

In one aspect of the invention, the $R^5$ and $R^6$ moieties are independently each an aryl that is optionally further substituted by halogen, $C_1$-$C_6$ alkyl, $C_1$-$C_6$ perfluoroalkyl, hydroxy, $C_1$-$C_6$ alkoxy, or $NO_2$. In another aspect of the invention, the $R^5$ and $R^6$ moieties are each phenyl or phenyl substituted one or more times by fluorine.

Either J and K, considered in combination, or K and L, considered in combination, are —$CH_2$— and form a three-membered cyclopropane ring fused to the cyclopentane ring of the formula. Where J and K, in combination, are —$CH_2$— the resulting compound has the formula:

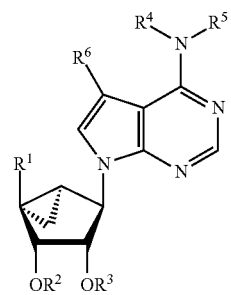

Similarly, where K, and L, in combination, are —$CH_2$— the resulting compound has the formula:

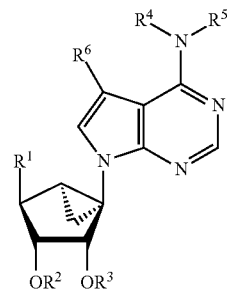

Where the substituents $R^1$-$R^6$ are as defined above.

In an alternative aspect, the disclosure is directed to adenosine kinase inhibitors wherein $R^1$ is methyl or hydroxymethyl, $R^2$ and $R^3$ are independently hydrogen or methyl, $R^4$ is hydrogen, and each of $R^5$ and $R^6$ is phenyl or substituted phenyl.

The adenosine kinase inhibitors of the present disclosure may alternatively be selected from compounds having the following formulae:

Compound 34

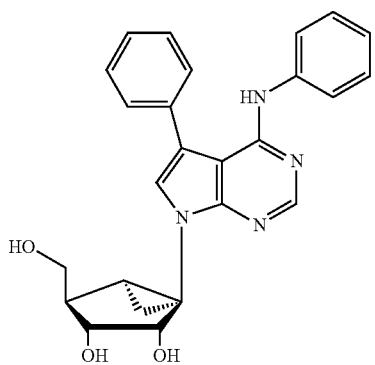

Compound 38a

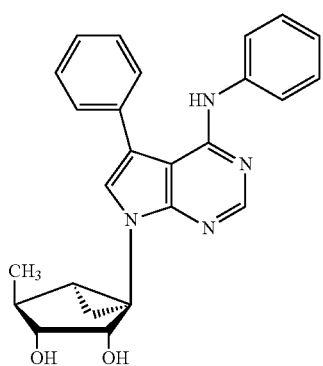

Compound 38b

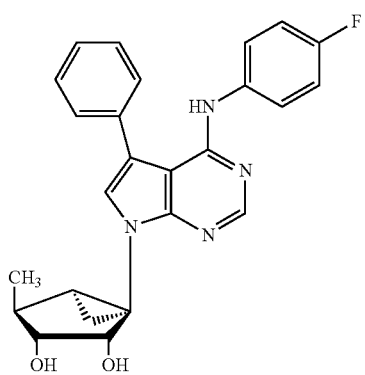

Compound 38c

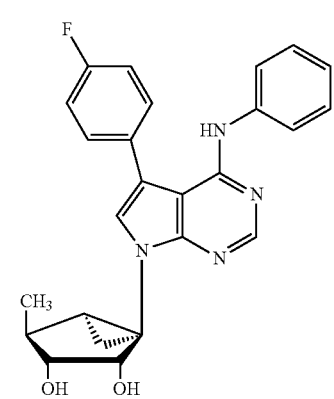

Compound 55

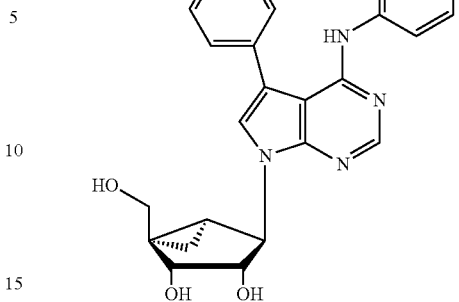

In some aspects, the disclosed adenosine kinase inhibitors may be incorporated into a pharmaceutical composition. That is, the disclosed inhibitors may be combined with one or more additional substances to facilitate the administration of the adenosine kinase inhibitors to a subject. For example, the adenosine kinase inhibitors may be present in a formulation that further includes one or more pharmaceutically acceptable carriers, excipients, preservatives, and/or diluents.

Pharmaceutically acceptable excipients may be selected to confer a therapeutic enhancement on the selected adenosine kinase inhibitor in its final dosage form, such as by facilitating drug absorption, reducing viscosity, or enhancing solubility, among other effects. Alternatively or in addition, excipients may possess utility for the manufacturing process, such as to aid in the handling of the adenosine kinase inhibitor for example by facilitating powder flowability or non-stick properties, aiding in vitro stability such as by preventing or minimizing denaturation or aggregation over an expected shelf life. The selection of appropriate excipients may also depend upon the route of administration and the dosage form.

The composition may be administered to a subject using any medically acceptable and effective technique. For example, the adenosine kinase inhibitor may be administered intravenously, orally, transdermally, subcutaneously, mucosally, intramuscularly, intranasally, intrapulmonary, parenterally, intrarectally or topically, without limitation. The disclosed pharmaceutical composition may be formulated to be fully compatible with a selected means of administering.

The adenosine kinase inhibitors of the present disclosure may be particularly useful when formulated so as to readily, or at least more readily, cross the blood-brain barrier. For example, the adenosine kinase inhibitor may be conjugated to one or more small molecules that confer brain-penetrant properties onto the molecule, such as one or more selected brain-penetrant peptides. Alternatively, or in addition, the adenosine kinase inhibitor may be administered in combination with one or more additional substances to facilitate passage of the inhibitor across the blood-brain barrier.

Where the adenosine kinase inhibitors of the present disclosure exhibit limited blood-brain barrier permeability, the adenosine kinase inhibitors may be administered directly to the patient via an by intracranial injection either acutely, or chronically via an infusion pump or other delivery device.

In yet another alternative aspect of the disclosure, administration of a selected adenosine kinase inhibitor may be considered during the course of a standard surgical resection of an epileptogenic focus, in order to prevent or moderate secondary postsurgical epileptogenesis. That is, the inhibitors of the disclosure may be administered during the course of another procedure during which the brain may be accessible. In such cases, administration of the adenosine kinase inhibitors may be performed within the context of a planned surgery.

Where the adenosine kinase inhibitor is being administered to the brain during a procedure, the inhibitor may be delivered by placing a drug-delivery substance in contact with the desired brain tissue, for example into a resectional cavity. Any appropriate drug-delivery substance may be used, for example such as a polymer that is a synthetic polymer, natural or artificial silk, and the like configured to release the selected adenosine kinase inhibitor over a desired time frame, such as days or even weeks. Administration of the adenosine kinase inhibitors via contact with a drug-delivery substance may permit the delivery of the inhibitor to a specific target area in the brain.

The present disclosure may also be directed to a method of preventing epilepsy and/or preventing its progression. The method includes administering an effective amount of the adenosine kinase inhibitors of the present disclosure to a subject in need thereof. An effective amount is that amount sufficient to produce a measurable decrease in the progression of epilepsy, or symptoms associated with epilepsy, in the subject. The method may include a method of preventing the recurrence of epilepsy in a patient by administering an adenosine kinase inhibitor of the present disclosure. Alternatively or in addition, the method may include inhibiting or suppressing epileptic seizures in a patient.

The present disclosure may additionally include methods of treating a disorder in a patient that may be characterized by pathological overexpression of adenosine kinase, such as for example Parkinson's disease, Alzheimer's disease, or cancer. Such methods may include administering an effective amount of the adenosine kinase inhibitors of the present disclosure to a subject sufficient to produce a measurable decrease in the symptoms associated with the disorder.

Discussion

The application of AdK inhibitors to CNS disorders such as epilepsy and chronic pain experienced a hiatus during the past decade, due to possible side effects of the known inhibitors. Critical gaps to be addressed are isoform selectivity (cytoplasmic versus nuclear AdK), cell-type selectivity (neuron versus astrocyte), and trans-membrane transport. Thus, there is a need for a new class of inhibitors with enhanced selectivities, such as nucleosides that have a major distinction from the known riboside inhibitors, such as 1a and 2.

An alternative ribose-like ring system, e.g. two isomeric methanocarba pseudoribose substitutions, has been utilized in nucleoside derivatives to demonstrate that inhibition of AdK is compatible with these major structural changes. By virtue of the bridged bicycloaliphatic ring, a rigid (S) 3'-exo or (N) 2'-exo envelope conformation is permanently locked in these nucleoside analogues. The most effective inhibitors, (S)-methanocarba derivatives 34, 38a, 38b and 38c and (N)-methanocarba derivative 55 were approximately two-fold less potent than the reference compound 2. The apparent discrepancy for the IC50 of 2 in our study of 48 nM, compared to its previously reported sub-nM IC50, is because of the use of a different assay system. The previous assay used was based on a radioactive assay using adenosine as a substrate, and ours is a commercial spectrophotometric assay based on inosine as substrate.

The presence of a p-F substitution in either the 5-phenyl 38b or 4-phenylamino 38c ring in the (S)-methanocarba series maintained the inhibitory potency of analogue 38a. We synthesized and compared potencies of two pairs of corresponding (S) and (N)-methanocarba 4'-$CH_2OH$ derivatives. We conclude that both conformations maintain potency at hAdK and can provide a path to novel nucleoside inhibitors. 5-Iodo analogues 32 (S) and 57 (N) displayed comparable potency, and the pair of more potent 4-phenylamino-5-phenyl analogues 34 (S) and 55 (N) also displayed similar IC50 values. This conclusion was consistent with X-ray structures of known inhibitors bound to hAdK[32], and with molecular docking and MD analyses of several of the present derivatives.

A similar attempt to constrain analogues of 2'-deoxy-nucleoside inhibitors of adenosine deaminase (ADA) using the [3.1.0]bicyclohexane ring system failed. Although the enzyme preferred the (N) methanocarba nucleoside over the (S), the relative rate of deamination was ~100-fold lower than adenosine, which suggested a possible role of the 4'-oxygen atom of native ribose in an anomeric effect to assist hydrolysis by ADA. In (S)-methanocarba nucleosides, the syn-conformation of the pseudoglycosidic bond is thought to be more stable than the anti-conformation, but in the X-ray structure of hAdK complexes, the nucleoside anti-conformation is present. The analysis of MD simulation starting from the X-ray complex suggests that the anti conformation suits at best the electrostatic potential distribution of the enzyme active site, featuring a highly hydrophobic cavity that hosts the purine core next to a region full of charged residues that anchors the ribose ring.

As far as the conformational preference of the enzyme is concerned, the active site of AdK appears to be highly flexible, as both (S)-methanocarba (C3'-exo, P=198°) compound 34 and its (N)-methanocarba (C2'-exo, P=342°) analogue 55 are equipotent inhibitors. It has to be noted that the synthesized locked conformers deviate by ±36° from the (N) and (S) conformations of the natural ribose counterparts. Interestingly, the near equipotency of (N) and (S) methanocarba isomers did not apply to conformationally locked analogues of 1a lacking the phenyl moieties. (S)-Conformers 30 and 49 were weak inhibitors of hAdK, while the inhibitory potencies of 1a and its (N)-methanocarba counterpart 57 were comparable. A possible explanation is provided by the modeling results: the bulky N6,C7-diphenyl substituents do not fit into the hAdK closed form and, as emerged from MD simulations, induced the opening of the small lid domain. The enzyme open conformation is expected to exhibit a higher plasticity with respect to closed conformation to which smaller 1a mimics are predicted to bind. As a consequence, this enzyme conformation could accommodate the pseudo-sugar ring locked in both the (S) and (N) conformations. Thus, hAdK might indeed prefer the (N)-conformer as inhibitor in the closed/catalytic-phase of the enzyme.

Thus, we have discovered novel high potency inhibitors of hAdK, which can now be evaluated in vivo, for example in effects on DNA methylation, in comparison to riboside inhibitors such as 1a. Although nucleosides often have low entry into the CNS, the slightly greater hydrophobicity of the (S)-methanocarba derivatives (c Log P of 49 is −0.11; tPSA is 120 Å) compared to ribosides (c Log P of the tetrahydrofuryl equivalent of 49 is −1.15; tPSA is 130 Å) might be beneficial for crossing the blood brain barrier. Furthermore, there remains the possibility that the specificity for AdK is enhanced in these (S)-methanocarba derivatives, which is crucial for avoiding possible side effects already noted for known AdK inhibitors. Although we have shown the feasibility of using this ribose conformational constraint in AdK inhibitors, there remains room for structural optimization to improve the inhibitory potency, considering that some of the known inhibitors achieve sub-nM affinity.

The interaction of these (S)-methanocarba analogues with nucleoside transporters that are relevant to adenosine derivatives, such as ENT1 and CNT2, remains to be characterized. The ability to serve as substrate or inhibitor of nucleoside transporters could affect the biodistribution or availability of the compounds in vivo. An analogue of the potent ENT1 inhibitor S-(4-nitrobenzyl)-thioinosine containing the opposite ring twist conformation ((N) methanocarba) was shown to inhibit ENT1, and other fixed conformations of 2'-deoxynucleosides were evaluated. (S)-Methanocarba 2'-deoxyadenosine inhibited both ENTs and CNTs, although less potently than 2'-deoxyadenosine.

The bioavailability and the in vivo activity of these inhibitors remain to be determined. Other nucleoside derivatives were protective in seizure models when administered peripherally. For example, the Br analogue of carbocyclic nucleoside 2 was found to be orally active in vivo in models of pain and inflammation. 5'-Deoxynucleoside analogues of 1a were noted to be more potent in vivo than 5'-amino analogues, possibly because of enhanced passage across the blood-brain barrier by virtue of being less polar. Among the new (S)-methanocarba AdK inhibitors, 5'-deoxy analogue 38a and especially the fluoro analogues 38b and 38c appear to be the least polar, based on their tendency to dissolve in organic solvents.

It is possible that transient treatment with AdK inhibitors would have long-lasting therapeutic benefits for treatment of CNS disorders, not only by raising the basal level of AR activation but also through epigenetic reprogramming. A high level of adenosine in the brain drives the enzymatic equilibrium in the presence of S-adenosylhomocysteine (SAH) hydrolase in the direction of increased SAH formation. SAH in turn inhibits DNA methyltransferases through product inhibition. Because the epigenetic effects related to changes in the DNA methylation status would persist, it might be possible to reduce the duration of drug administration, thus avoiding toxicities associated with prolonged, chronic dosing. A transient dosing regimen might also avoid possible side effects, such as liver toxicity. Compound 38a was submitted to the Psychoactive Drug Screening Program (PDSP) for screening at 45 receptors, channels and transporters. It was found to inhibit radioligand binding at the human 5HT7 (serotonin) receptor with a Ki value of 0.71 µM and did not substantially inhibit binding at any of the other off-target sites examined (<50% inhibition at 10 µM). Also, 38a was found to be inactive (10 µM) as agonist or antagonist at human P2Y1, P2Y2, P2Y4, and P2Y11Rs (calcium transients) expressed in 1321N1 astrocytoma cells and protease-activated receptor (PAR)1 expressed in mouse KOLF cells. Nevertheless, the offtarget interactions of the present set of compounds would have to be examined more extensively.

In conclusion, the development of novel AdK inhibitors, by virtue of their ability to raise the level of endogenous adenosine, particularly in disease states, remains of interest for the potential treatment of seizures and neurodegenerative and inflammatory conditions. We demonstrated that the class of constrained bicyclic ribonucleoside analogues retain inhibitory activity at this enzyme and are amenable to structural modification to enhance the potency. The SAR for ring-constrained analogues roughly parallels the SAR determined previously for ribosides, but analogues with aryl groups at the 7-deaza and $N^6$ positions of adenine are greatly favored, with (S)≈(N). We determined that the (S) conformation permits a range of substitutions, but amino derivatives 45 and 49 were much less potent than expected from the ribose equivalents. However, a difference between the (N) and (S)-methanocarba series is that the methanocarba equivalent of reference riboside 1a is more potent in the (N) than in the (S) series. We have identified compounds 34, 38a, 38b, 38c, and 55 as hAdK inhibitors with IC50 values of ~100 nM. The successful docking of selected members of this series in the enzyme structure suggests that a structure-based design approach for further enhancement is possible. Although we have not yet explored all of the potential off-target effects and adenosine-receptor related side effects of this structural class, it is possible that the novel non-ribose ring system will provide a cleaner pharmacological profile. The potent AdK inhibitors in this study are now ready for further tests in animal models of epilepsy and its development.

Synthesis of Adenosine Kinase Inhibitors

Figure 2:
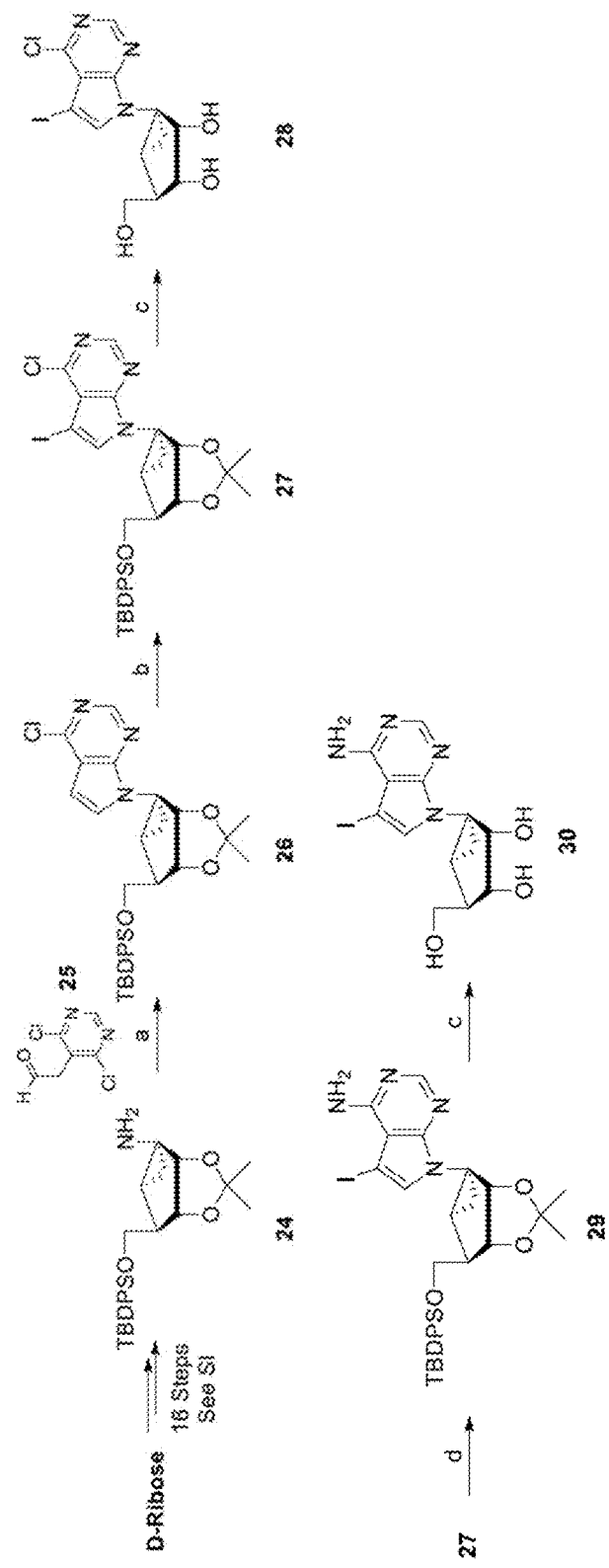
FIG. 2: A first portion of a synthetic scheme for the synthesis of nucleobase modified (S)-methanocarba analogues of 5-iodotubercidin. Reagents and conditions: (a) EtOH, 2-(4,6-dichloropyrimidin-5-yl)acetaldehyde (25), NEt$_3$, reflux, 18 h, 76%; (b) anhydrous DMF, NIS, 60° C., 6 h, 92%; (c) 70% TFA (aq), rt, 1.5 h, 27-83%.
Figure 3:
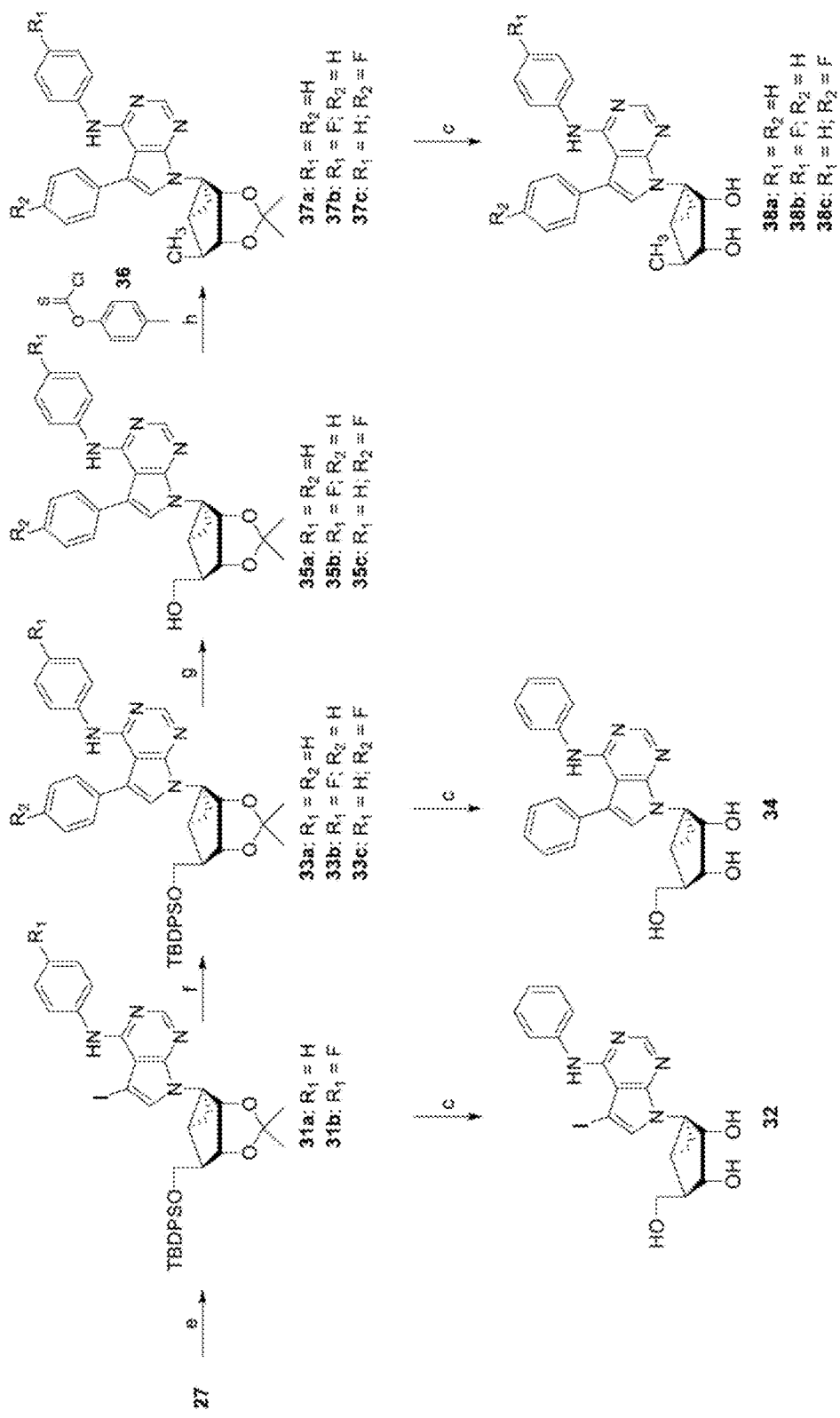
FIG. 3: A second portion of a synthetic scheme for the synthesis of nucleobase modified (S)-methanocarba analogues of 5-iodotubercidin. Reagents and conditions: (d) EtOH, 7N NH$_3$-MeOH, sealed tube, 110° C., 18 h, 89%; (e) anhydrous THF, aniline, 1M tBuOK in THF, −20° C., 1.5 h, 70-80%; (f) 6:1 DME-EtOH, phenylboronic acid, Pd (PPh$_3$)$_4$, sat. Na$_2$CO$_3$ (aq), 90° C., 7 h, 75-86%; (g) anhydrous THF, 1M TBAF in THF, rt, 18 h, 85-96%; (h) (i) anhydrous CH$_3$CN, DMAP, O-(p-tolyl) chlorothionoformate (36), rt, 18 h; (ii) anhydrous toluene, Bu$_3$SnH, AIBN, reflux, 2 h, 52-90%.

The intermediate 24 containing the (S)-methanocarba ring with 1'-amino functionalization was required as an intermediate for the target compounds (see the reaction scheme of FIGS. 2 and 3). We adapted our previously reported synthesis of enantiomerically pure (S)-methanocarba nucleosides via bicyclic intermediate 24, to a larger scale preparation of this intermediate. The major modification over the previously reported route was the use of acetone cyanohydrin/LiH combination in place of lithium cyanide in a synthetically challenging 10th step. This led to a considerably higher ratio of product to byproduct for this step and resulted in the key intermediate 24 with 0.04% overall yield over 16 steps. The yield was largely limited by the low yield of the isopropylidene isomerization in step h, which was only 11% (barring that the total yield would be 0.34%). Other contributing low yield steps were d, f, g and n.

Using the (S)-methanocarba intermediate 24 as a precursor, analogues of known AdK nucleoside inhibitors were prepared. The 7-deazaadenine core was constructed by reacting 24 with symmetrical dichloropyrimidine bearing an acetaldehyde moiety (25), which on iodination using NBS followed by the removal of protecting groups in aqueous trifluoroacetic acid resulted in 28. Similarly, the aminolysis of 27 and deprotection rendered 30, the (S)-methanocarba analogue of 1a, in moderate yield.

Substitution of chlorine on the 6-position of 7-deazapurine using aniline and sodium acetate achieved a complete reaction, but the use of a stronger base i.e. potassium tert-butoxide at lower temperature produced $N^6$-phenyl derivatives 31a and 31b in increased yields. A Suzuki reaction involving arylboronic acids and 31a,b, followed by the removal of a silyl protecting group gave 35a-c, which were subjected to Barton-McCombie deoxygenation to yield 5'-deoxy compounds 37a-c. Removal of the protecting groups from 31, 33 and 37a-c gave 32, 34 and 38a-c, respectively, in low to moderate yields. Compounds 38b and 38c differ from 38a only in the presence of a fluorine atom in the p-position of either the 4-phenyl-amino or 5-phenyl ring, respectively.

Figure 4:
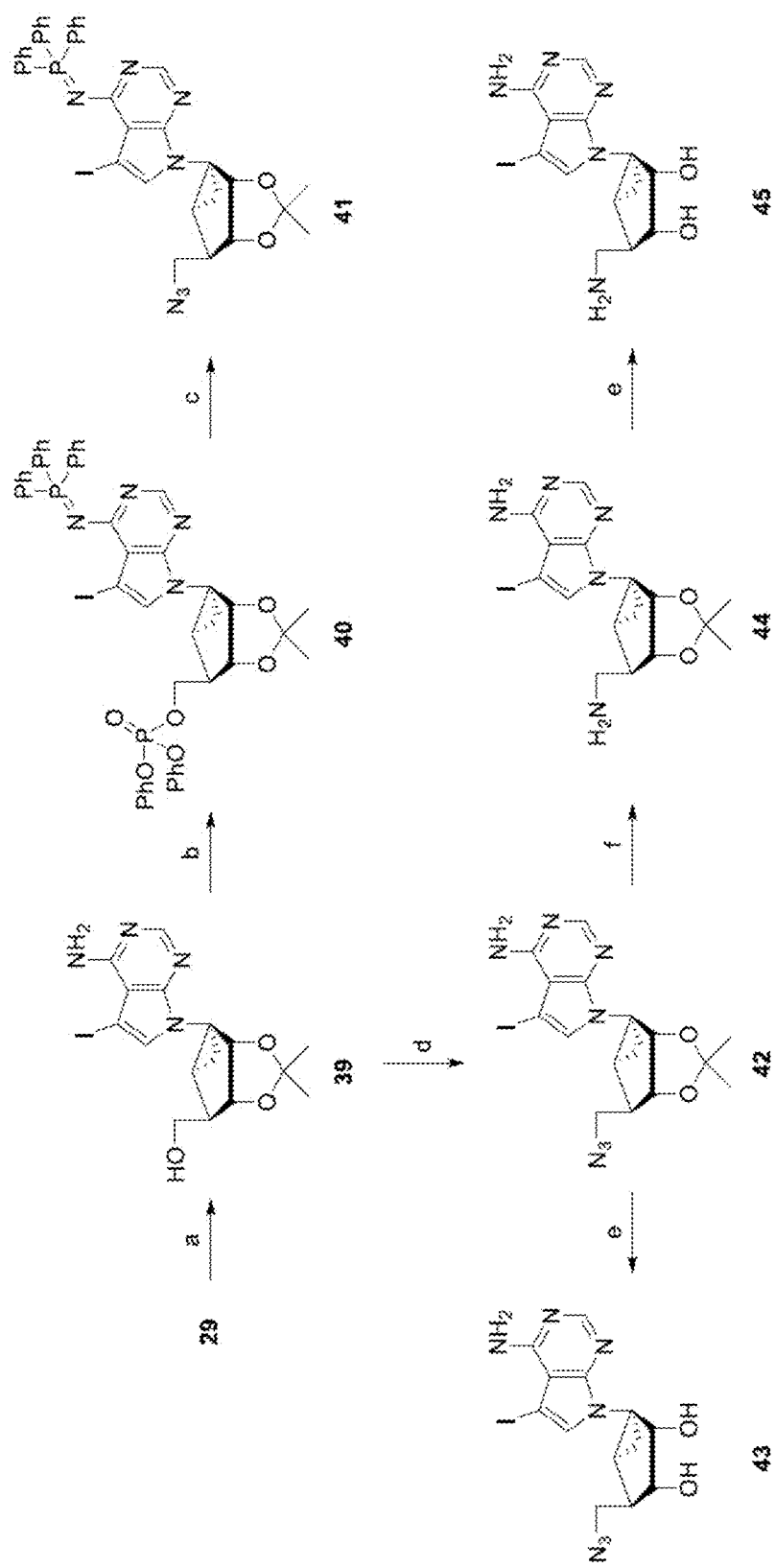
FIG. 4: A first portion of a synthetic scheme for the synthesis of 4'-position modified (S)-methanocarba analogues of 5-iodotubercidin. Reagents and conditions: (a) anhydrous THF, 1M TBAF in THF, rt, 18 h, quantitative yield; (b) anhydrous THF, PPh$_3$, DEAD, DPPA, 0° C.→rt, 18 h; (c) anhydrous DMF, NaN$_3$, 65° C., 24 h; (d) (i) anhydrous pyridine, MsCl, 0° C.→rt, 4 h (ii) anhydrous DMF, NaN$_3$, 65° C., 4 h, 95%; (e) 70% TFA (aq), rt, 1.5 h, 35-42%.

In an attempt to synthesize 5'-azido compounds (see FIGS. 4 and 5), a Mitsunobu reaction involving diphenylphosphoryl azide (DPPA) and 29 yielded disubstituted 40 exclusively. Surprisingly, this compound was sufficiently stable to be isolated using silica-gel column chromatography. 40 on heating with sodium azide in DMF formed undesired product 41, and attempts to convert this phosphine to 42 or 43 using aqueous TFA were unsuccessful. Alternatively, tosylation of 29 followed by substitution with sodium azide at elevated temperature afforded the desired compound 42 in 96% yield, which under Staudinger reaction conditions gave 44 in good yield. The de-protection of the acetonide group from 42 and 44 using aqueous TFA led to 5'-azido and 5'-amino congeners 43 and 45, respectively.

To arrive at 49 from 39, a Curtius rearrangement strategy was adapted, and to realize this, the 4'-hydroxylmethyl group in 39 was converted to the corresponding carboxylic acid 46 employing a TEMPO-BAIB oxidation in aqueous acetonitrile. Initial efforts to prepare the Boc-protected analog of urethane 48 from 46 using DPPA and tert-butanol failed, but instead, after deprotection of the isopropylidine group, resulted in dimer 47. However, a similar reaction with benzyl alcohol formed Cbz-protected compound 48, which on deprotection using 33% HBr in acetic acid provided the desired compound 49, as a minor product, and 50 as the major product. Unfortunately, an attempt to convert 50 to the desired compound 49 using NIS in DMF at elevated temperature did not materialize.

Figure 6:
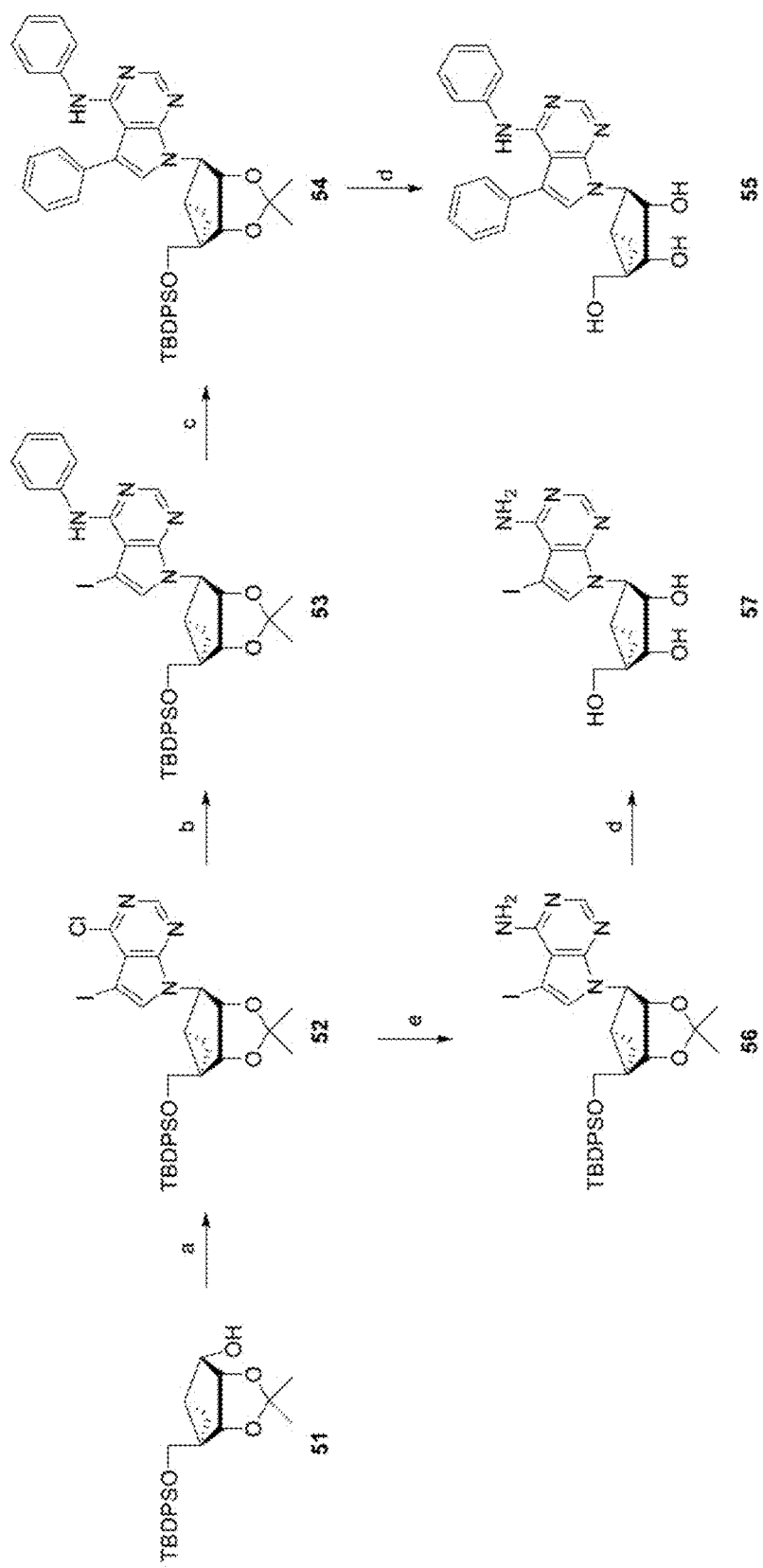
FIG. 6: Synthetic scheme for the synthesis of an (N)-methanocarba analogue 57 of 5-iodotubercidin and its N$^6$,7-diphenyl congener 55. Reagents and conditions: (a) 6-chloro-7-iodo-7-deazapurine, anhydrous THF, DEAD, PPh$_3$, 0° C.→rt, 18 h, 88%; (b) anhydrous THF, aniline, 1M tBuOK in THF, −20° C., 1.5 h, 63%; (c) 6:1 DME-EtOH, phenylboronic acid, Pd(PPh$_3$)$_4$, sat. Na$_2$CO$_3$ (aq), 90° C., 7 h, 82%; (d) 70% TFA (aq), rt, 1.5 h, 77-79%; (e) EtOH, 7N NH$_3$-MeOH, sealed tube, 110° C., 18 h, 82%.

The synthesis of several corresponding (N)-methanocarba analogues was performed as shown in FIG. 6. A protected bicyclic intermediate 51, prepared previously for studies of adenosine receptors, was subjected to a Mitsunobu reaction with 6-chloro-7-iodo-7-deazapurine. The next step provided two divergent pathways leading to target inhibitors: nucleophilic substitution of the 4-chloro group with either ammonia or aniline (followed by a Suzuki coupling at the 5-position). Deprotection of the hydroxyl groups yielded compounds 55 and 57, which are the (N)-methanocarba equivalent of compounds 34 and 30, respectively.

Biochemical Evaluation of Adenosine Kinase Inhibitors

Figure 7:
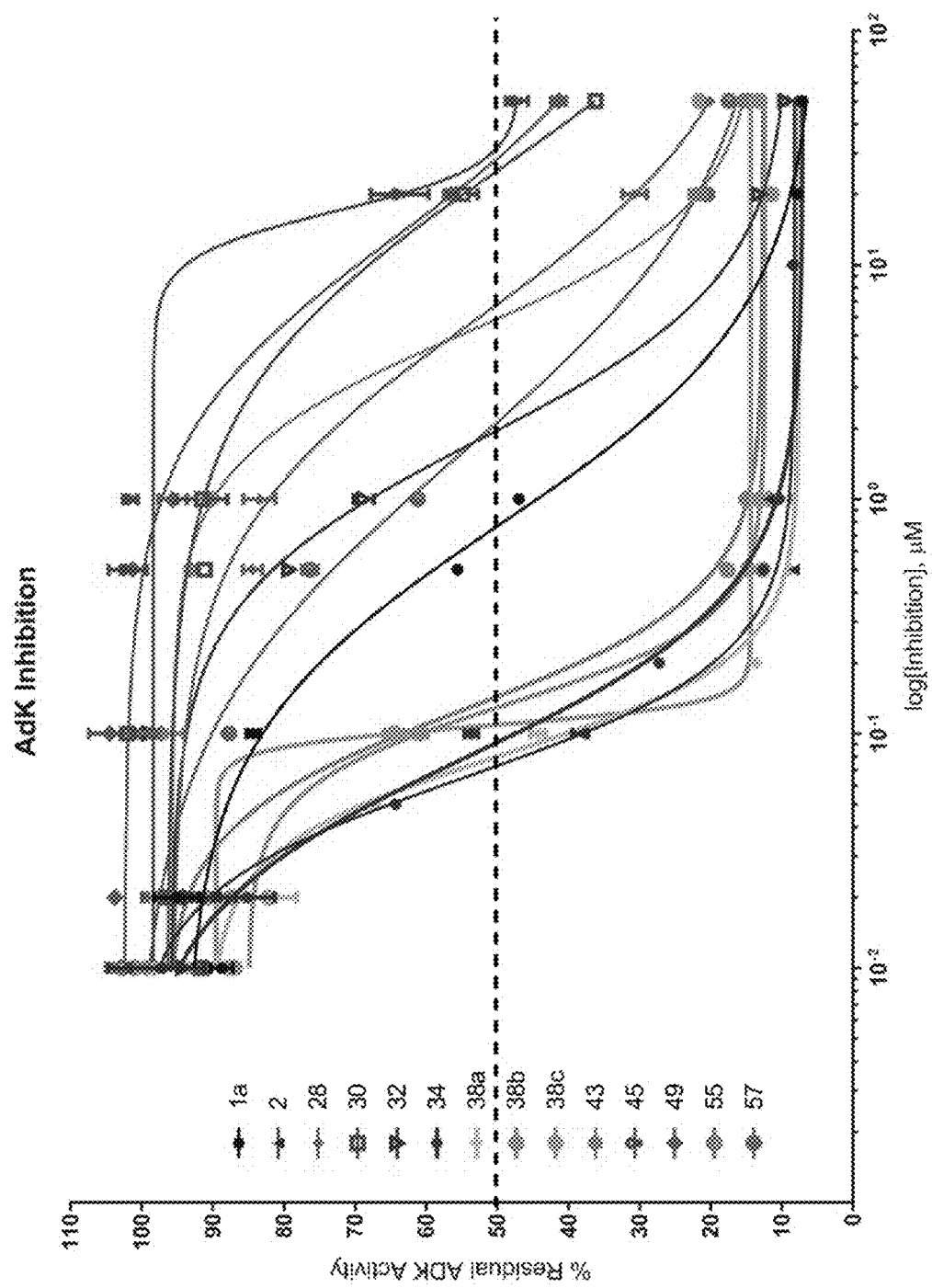
FIG. 7: A plot showing a concentration-response study for all inhibitors compared to 1a and 2 at 50 µM, 20 µM, 1 µM, 500 nM, 100 nM, 20 nM and 10 nM. Percent residual activity of 38a was commensurate with 2 at most concentrations. Slope activity was determined between 0-40 min of assay activity time and determined as a percentage relative to DMSO.

The nucleoside derivatives were tested for inhibitory activity at hAdK using a commercial, nonisotopic assay for the measurement of hAdK kinetic activity based on continuous monitoring of enzymatic activity at 340 nm (appearance of reduced nicotinamide-adenine dinucleotide from a coupled enzymatic reaction). The hAdK-catalyzed phosphorylation of inosine to inosine 5'-monophosphate is coupled to the inosine 5'-monophosphate dehydrogenase-dependent oxidation of the product. Thus, the assay was performed in the presence of dithiothreitol, oxidized nicotinamide-adenine dinucleotide (NAD, 2.5 mM) and ATP (2.75 mM) as cofactors and inosine (2.5 mM) as substrate. hAdK activity was continuously measured via absorption at 340 nm for four hours where measurements were made at five min intervals; however, for graphing and analysis purposes we focused on the first 40 min of activity, which is mostly linear, for determining slope activity as percent of AdK activity without the addition of any inhibitor (See FIG. 7). Percent inhibition of hAdK activity was calculated by determining the slope of the hAdK reaction during the linear phase of the enzymatic reaction (first 40 min) (see Table 1, below). We included two known AdK inhibitors, compound 1a and 2, as positive controls. Each inhibitor was analyzed at the following concentrations (µM): of 50, 20, 1, 0.50, 0.10, 0.020 and 0.010. Percent residual hAdK activity showed a significant interaction ($F_{78,490}=71$, $p<0.0001$) and main effects for both inhibitor ($F_{13,490}=626$, $p<0.0001$) and concentration ($F_{6,490}=3366$, $p<0.0001$). Post hoc analysis used Bonferroni multiple comparison tests to determine drug differences relative to 2 (most effective known inhibitor) at each of the concentrations investigated. At the highest concentration, 28, 30, 45, 49, and 57 significantly varied from 2 with poor inhibition of hAdK activity slope. Compound 43 was slightly more effective, varying from 2 at 20 µM. 32 and 55 were moderately effective, beginning to vary from 2 at 1 µM and 500 nM, respectively. Only at a concentration of 100 nM did the inhibition by 34, 38b, and 38c differ from 2, while 38a never significantly varied from 2, indicating that 38a as low as 20 nM was equipotent to 2 in inhibition of hAdK. At lower concentrations 34 and 38a maintained more potent hAdK inhibition; therefore, it was necessary to determine full concentration-response curves to distinguish between the most potent compounds. We performed a detailed concentration-response study of most of the analogues for precise determination of IC50, using the earlier data with the addition of three concentrations (10, 0.20 and 0.050 µM). The IC50 values for potent (S)-methanocarba inhibitors 34 and 38a were 114 and 88 nM, respectively.

TABLE 1

Percent inhibition values for all 14 hAdK inhibitors relative to uninhibited (DMSO) activity at the 50 µM, 20 µM, 500 nM, and 100 nM concentrations and $IC_{50}$ values.

| Compound | Inhibition at concentration indicated,[a] mean % ± SEM | | | | $IC_{50}$ (µM) + SEM |
|---|---|---|---|---|---|
|  | 50 µM | 20 µM | 500 nM | 100 nM |  |
| Control | 0 | 0 | 0 | 0 | ND |
| 1a, 5-IT | 88.3 ± 0.3 | 88.3 ± 0.3 | 44.4 ± 0.8 | 21.5 ± 0.9 | 0.82 ± 0.03 |
| 2 | 88.4 ± 0.3 | 88.3 ± 0.3 | 86.7 ± 0.2 | 59.0 ± 1.3 | 0.048 ± 0.001 |
| (S)-Methanocarba nucleosides | | | | | |
| 28 | 76.5 ± 0.9 | 68.9 ± 0.8 | 15.6 ± 1.4 | 6.6 ± 1.7 | 6.01 ± 0.18 |
| 30 | 58.2 ± 1.7 | 41.7 ± 0.9 | 8.8 ± 0.9 | 1.1 ± 2.1 | ND |
| 32 | 85.1 ± 0.6 | 80.9 ± 0.2 | 20.7 ± 0.8 | 2.9 ± 1.9 | 3.34 ± 0.19 |
| 34 | 88.3 ± 0.4 | 88.1 ± 0.3 | 82.2 ± 0.4 | 41.0 ± 1.2 | 0.114 ± 0.002 |
| 38a | 88.1 ± 1.5 | 88.4 ± 0.4 | 86.0 ± 0.3 | 49.7 ± 1.0 | 0.088 ± 0.003 |
| 38b | 86.9 ± 0.3 | 88.0 ± 0.3 | 85.2 ± 0.3 | 39.0 ± 1.2 | 0.110 ± 0.003 |
| 38c | 78.4 ± 0.7 | 88.6 ± 0.2 | 87.3 ± 0.3 | 35.6 ± 1.3 | 0.120 ± 0.003 |
| 43 | 80.5 ± 0.8 | 75.1 ± 0.5 | 6.8 ± 0.7 | 6.1 ± 3.8 | 5.38 ± 0.10 |
| 45 | 50.9 ± 1.1 | 36.0 ± 1.4 | −2.0 ± 2.7 | 8.4 ± 1.9 | ND |
| 49 | 60.4 ± 0.8 | 44.9 ± 0.7 | −1.3 ± 1.7 | −5.8 ± 2.0 | ND |
| (N)-Methanocarba nucleosides | | | | | |
| 55 | 85.4 ± 0.5 | 88.0 ± 0.2 | 82.3 ± 0.5 | 35.5 ± 1.4 | 0.14 ± 0.01 |
| 57 | 82.5 ± 0.3 | 79.5 ± 0.4 | 23.6 ± 1.1 | 12.3 ± 0.4 | 2.24 ± 0.04 |

[a] based on slope of the linear portion (0-40 min interval) of the activity plot of hAdK, compared to control with DMSO vehicle.
ND, not determined.

Because the 5'-OH derivative 30 was a poor inhibitor of hAdK, we hypothesized that it might serve as a substrate for hAdK, unlike the corresponding riboside 1a, which is not primarily a substrate. The Km of adenosine as substrate of hAdK is 700 nM, and the nucleoside analogue concentrations that we used in inhibition experiments far exceeded that concentration. By comparison in another kinase system, (S)-methanocarbathymidine, but not (N)-methanocarbathymidine, is a good substrate for herpes simplex virus type 1 thymidine kinase. Moreover, (S)-methanocarbathymidine is not a substrate for human cytosolic thymidine kinase isoenzyme 1. Thus, it was important to probe the substrate qualities of compound 30, (S)-methanocarbaadenosine derivative, at hAdK. Therefore, we performed three different assays under similar conditions: first, with substrate in the presence of 1 μM 30; second, without substrate in the presence of 1 μM 30; and third as a control, without 30. After 4 h incubation, the resulting mixtures were studied using LC-MS in negative and positive mode (Supporting information), which could identify and qualitatively measure the 7 levels of nucleosides and their phosphorylated products. In the first and last cases, we detected the final enzymatic product, i.e. xanthosine-5'-phosphate (MW 364+1). However in the first two cases, we found no evidence from the LC-MS analysis that 30 serves as a substrate of hAdK. There was a prominent signal (MW 402+1) from unchanged compound 30, and no detectable or prominent signal of the corresponding 5'-phosphate (MW 482±1).

Molecular Modeling

The selection of novel AdK inhibitors was informed using molecular modeling studies. To date, three X-ray structures of the hAdK in complex with both nucleoside and non-nucleoside inhibitors have been solved, which revealed at least two different enzyme conformations. A closed form was observed for the complexes of hAdK with 1c (PDB ID: 2I6A) and 7-ethynyl-7-deazaadenosine (PDB ID: 4O1L), but the enzyme adopted an open conformation in the complex with a bulkier alkynylpyrimidine inhibitor (PDB ID: 2I6B). Given the structural similarity of our compounds to 1c, we used the corresponding co-crystallized structure as macromolecular starting point of our analysis.

MD Simulation of the X-Ray Complex.

In a first instance, we subjected the experimentally determined complex (PDB ID: 2I6A) to 30 ns of all atom Molecular Dynamics (MD) simulation, in order to identify the residues mostly involved in the interaction and to explore in detail the conformational space of the inhibitor. In the starting structure, 1c bound with the glycosidic bond ($\chi$) in the anti conformation ($\chi$=−134.7°) and the sugar moiety in the C1'-exo conformation (P=125.3°). The analysis of the trajectory revealed that the anti conformation was retained throughout the simulation, while the pseudo-sugar ring explored different conformational states. The anti conformation of the glycosidic bond seemed to be compatible with the charge distribution of the residues surrounding the enzyme active site. Indeed, the inhibitor established persistent H-bond interactions with negatively charged residues through the C2' and C3' hydroxyl groups and a stable π-π stacking interaction with Phe170 through the purine core. Concerning the ribose ring conformations, the starting C1'-exo conformation featuring a bidentate H-bond interaction between the C2' and C3' hydroxyl groups and the sidechain of Asp18 was the most favorable in terms of ligand-protein interaction energy (IE) during the simulation. However, after approximately 12 ns of MD simulations, the H-bond network was lost, and the pseudo-sugar ring adopted a C2'-endo (S) conformation (P=156.7°, Figure S2 ii) with the C2' and C3' hydroxyl groups interacting with the Asp18 sidechain and water molecules, respectively. At the end of the simulation, the ring adopted a less favorable—in terms of IE—C3'-endo (N) conformation (P=36.4°, Figure S2 iii) that was accompanied by a rotameric switch of the Asp18 sidechain to establish a bidentate H-bond interaction with Arg132 while still interacting with the C3' hydroxyl group (data not shown). To assess whether this conformation was persistent, we restarted the simulation for another 30 ns in which the inhibitor remained in the (N) conformation. These results prompted us to consider nucleoside inhibitors constrained by the methanocarba ring system in the (N) as well as the (S) conformation. We therefore analyzed from a molecular point of view the comparison between two selected isomers, namely 34 and 55.

Docking of Selected Methanocarba-Nucleoside Derivatives.

The compounds were docked into the closed form of hAdK by using the Induced Fit Docking (IFD) procedure, because a preliminary attempt to dock the structures into the rigid enzyme in the closed form failed. In both docking poses (see FIGS. 8A and 8B), the purine core established a π-π stacking interaction with Phe170 and H-bond interactions with the sidechain of Asn14 and the backbone of Ser65, through the N1 and N3 atoms, respectively. Furthermore, the phenyl rings interacted with residues located in the small lid domain (Leu16, Leu40, Leu134, Ala136, Leu138, and Val174) by means of extended hydrophobic contacts. The methanocarba ring bound with different orientations for the two isomers: in the docking pose of 34 (See FIG. 8A) the C2' and C3' hydroxyl groups established a bidentate H-bond interaction with the sidechain of Asp18 while interacting also with the backbone of Gly64 and the sidechain of Asn68, respectively. In the docking pose of 55 (FIG. 8B), the network of H-bond interactions was more extended and involved other residues beyond Asp18 and the C5' hydroxyl group. In particular, the hydroxyl groups in C2', C3', and C5' engaged in H-bond interactions with Gly64 (backbone) and Asn68, Arg332, and Asn296, respectively.

MD Simulations of Methanocarba-Nucleoside hAdK Complexes.

Figures 9A, 9B:
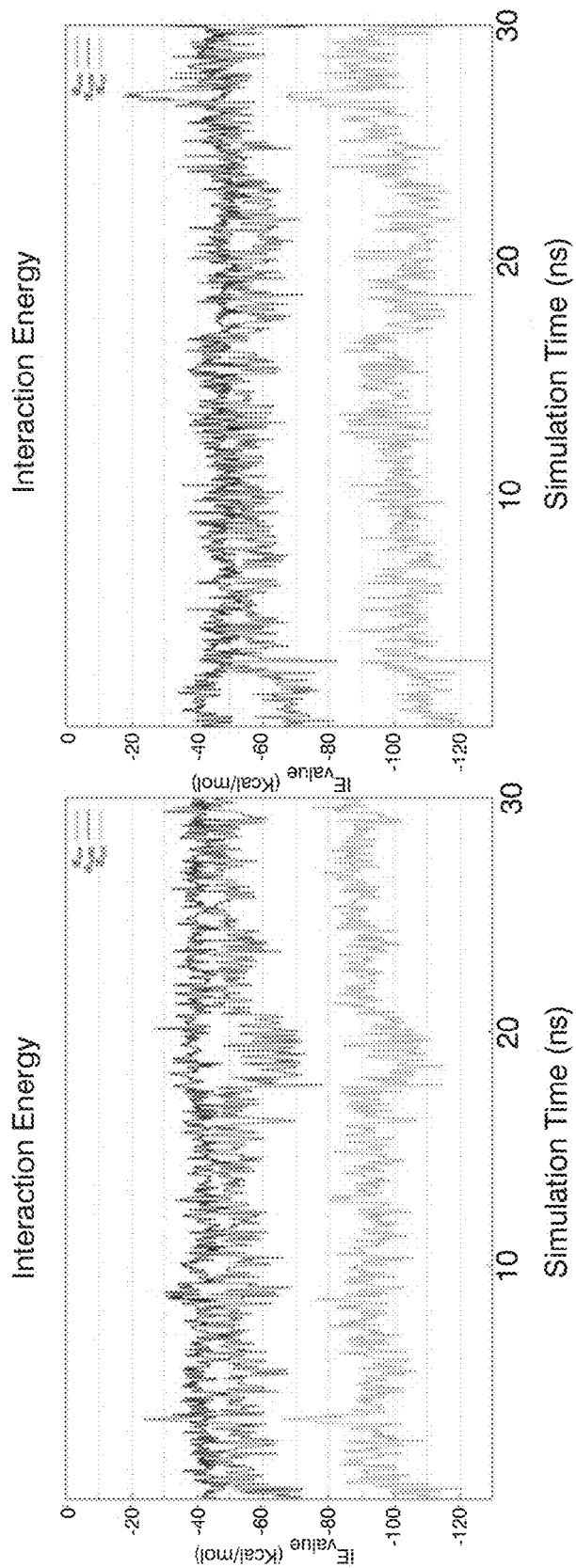
FIGS. 9A-9B: The IE profiles during 30 ns of MD simulations of the hAdK in complex with compounds 34 (FIG. 9A) and 55 (FIG. 9B) starting from the docking poses shown in FIG. 8. The electrostatic (IEele) and van der Waals (IEvdW) contributions and the total IE (IEtot) are represented as blue, green and pink lines, respectively. IE values are in Kcal/mol.

The docking poses described above were subjected to 30 ns of all-atom MD simulation, and the corresponding IE profiles are reported in FIGS. 9A and 9B. The visualization of the trajectory of the 34-hAdK complex, revealed that the bidentate H-bond interaction with Asp18 was maintained throughout the simulation also through the interplay of Asp300, Arg332, and water molecules that contributed to maintaining the hydroxyl groups and the Asp18 sidechain in a reciprocal favorable orientation. On the contrary, due to the opening of the small lid domain during the simulation (see below), the H-bond network around the C5' hydroxyl group was lost, and protein residues were replaced with water molecules. The aromatic moieties of inhibitor 34 were stabilized by π-π stacking interactions with Phe170 (purine core) and Phe201 (phenyl-amino group), and van der Waals interactions with the sidechain of Gln38 (phenyl group). The analysis of the trajectory of the 55-hAdK complex featured less enduring H-bond networks and more predominant van der Waals interactions that contributed to a net IE profile that was slightly more favorable (FIG. 9B). In particular, in addition to the interaction already described for the complex with 34, the phenyl-amino group of 55 was stabilized by van der Waals interactions with Leu40 and Leu138.

hAdK Conformation During MD Simulations.

As mentioned above, initial attempts to dock the methanocarba ligands in the closed conformation of the enzyme failed. We therefore resorted to an IFD protocol to obtain initial docking poses that we subsequently subjected to MD simulation. The analysis of the trajectories revealed that after a few ns of simulation, in both cases the opening of the small lid domain occurred. Superimposition of MD average protein structures with the enzyme in the closed (PDB ID: 2I6A) and open (PDB ID: 2I6B) conformation, revealed that while the enzyme remained in the closed conformation for the 1c-hAdK complex, in the complexes with 34 and 55 the enzyme approached an open conformation. In particular, in the MD average structures the small lid domain was rotated outward by about 24° with respect to the large domain for both the 34-hAdK and 55-hAdK complexes (comparison with the enzyme starting structure obtained after IFD), while the rotation angle was approximately 9° for the 1c-hAdK complex. The preference for an open enzyme conformation as well as the rotation angle of the small lid domain during MD simulations of nucleoside inhibitors agreed with modeling studies reported by other authors.

Epigenetic Activity in ADK-L Cells.

Figure 10:
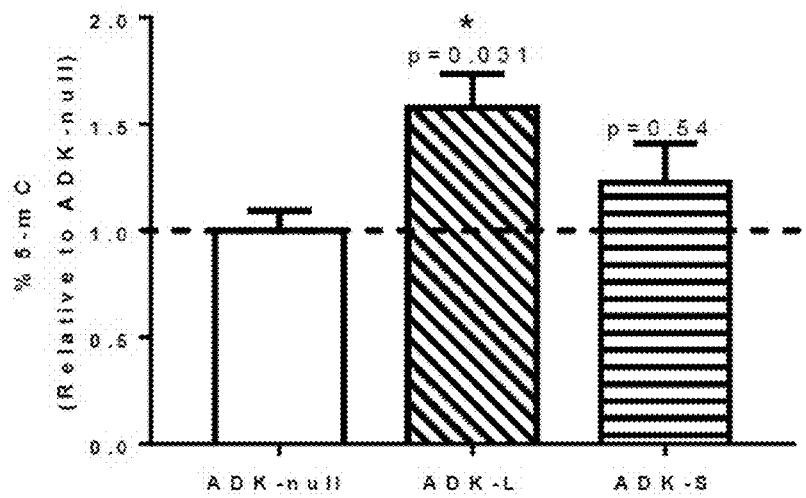
FIG. 10: A plot showing that DNA methylation is significantly increased in ADK-L cells vs. ADK-null cells, and that ADK-S does not significantly affect DNA methylation.

As a secondary screening tool we engineered BHK cell lines that stably overexpress either the nuclear isoform ADK-L or the cytoplasmic isoform ADK-S in an ADK-null background. We show that overexpression of ADK-L results in >50% increase in baseline DNA methylation (see FIG. 10), whereas overexpression of ADK-S was without a statistically significant effect.

Next, we tested whether known ADK inhibitors, as well as compound 55 and compound 38A differ in the specificity of ADK-L vs. ADK-S.

ADK-L cells were treated for 24 hours with vehicle or the ADK inhibitors 5-iodotubercidin (5-ITU, 26 nM), ABT-702 (1.7 nM), A-134974 (60 μM), compound 55 (26 nM), or compound 38a (26 nM). The in vitro IC50 for each conventional ADK inhibitor was selected as the treatment dose. Compounds 55 and 38a were used at equimolar concentrations to 5-ITU. Purified genomic DNA (100 ng) was run on a 5-methylcytosine (5 mC) ELISA. Data shown in FIG. 11 are represented as the mean±SEM (n=8-9) and analyzed by one-way ANOVA followed by Tukey's multiple comparisons test (C) or Krus-kal-Wallis test followed by uncorrected Dunn's test with all comparisons relative to ADK-L vehicle (D).

Figure 11:
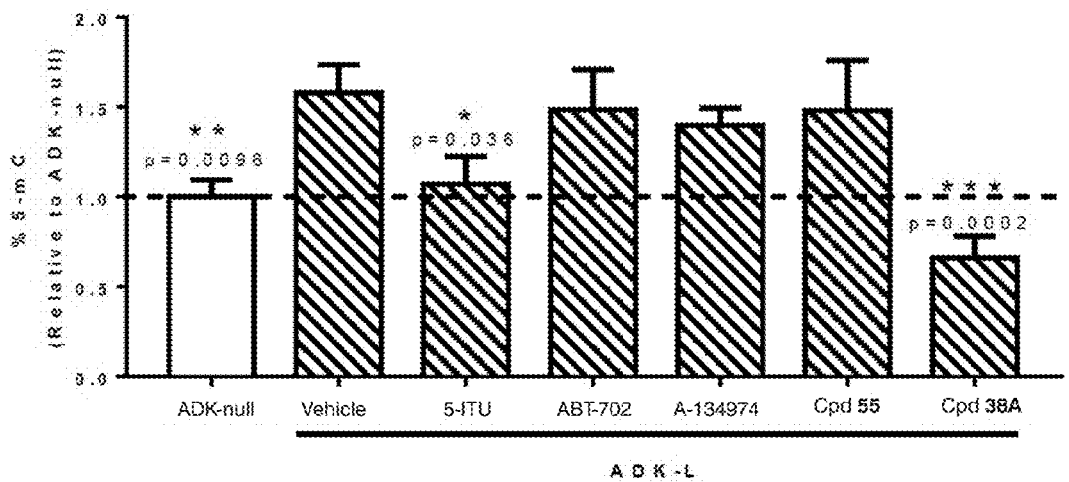
FIG. 11: A plot showing that at equimolar concentrations the nucleoside inhibitor 5-ITU as well as compound 38A reduce DNA methylation in ADK-L cells by >35% and >50%, respectively, whereas none of the other inhibitors was effective.

FIG. 11 shows that at equimolar concentrations the nucleoside inhibitor 5-ITU as well as compound 38A reduce DNA methylation in ADK-L cells by >35% and >50%, respectively, whereas none of the other inhibitors was effective. None of the inhibitors triggered any significant decreases in DNA methylation in ADK-S cells (not shown). These data demonstrate that compound 38A reduces DNA methylation specifically in ADK-L cells and show that compound 38A has more potent epigenetic effects than 5-ITU. These data suggest that the South (S) configuration of compound 38A confers specificity to ADK-L whereas the North (N) configuration of compound 55 was not active.

No Off-Target Activity in Adk-Null Cells.

To test for nonspecific activities of ADK inhibitors on DNA methylation, we tested our set of inhibitors on ADK-null cells, which are hypomethylated and can be used to identify treatments that increase DNA methylation (whereas ADK-L cells display a hypermethylated ceiling effect). The results are shown in FIG. 12, with data presented as the mean±SEM (n=4-9) and analyzed by one-way ANOVA then uncorrected Fisher's LSD test with all comparisons relative to vehicle treatment.

Figure 12:
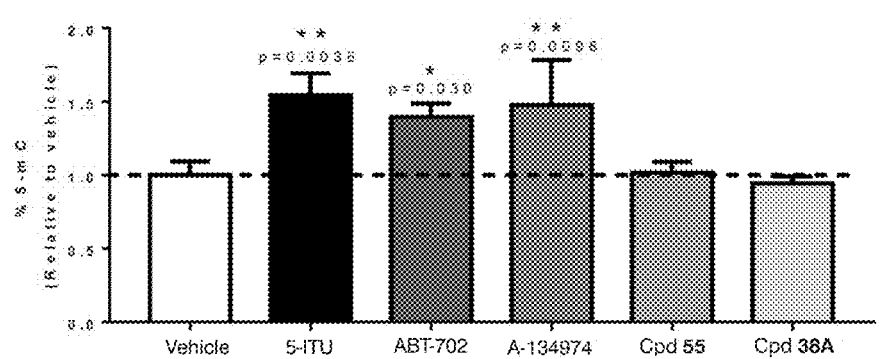
FIG. 12: A plot showing DNA methylation assessed in ADK-null cells treated with vehicle or ADK inhibitors. Due to their non-specific effects 5-ITU, ABT-702 and A-134974 significantly increased DNA methylation vs. vehicle, while compounds 55 and 38a exhibit greater specificity.

As shown in FIG. 12, in contrast to the established ADK inhibitors 5-ITU, ABT-702, and A-134974, which all showed non-specific (i.e. in the absence of any ADK expression in ADK-null cells) increases in DNA methylation, the ADK-inhibitors compounds 55 and 38A had no effect on DNA methylation, demonstrating specificity and lack of epigenetic off-target effects. Compound 38A therefore exhibits highly specific epigenetic activity attributable to ADK-L inhibition.

Epigenetic activity in the brain. Swiss Webster mice received 3 i.p. doses of vehicle, 5-ITU (3.1 mg/kg) or compound 38a (3.1 mg/kg) once every 12 hours. Tissue was harvested 1 hour after the 3rd dose.

Figures 13A, 13B, 13C:
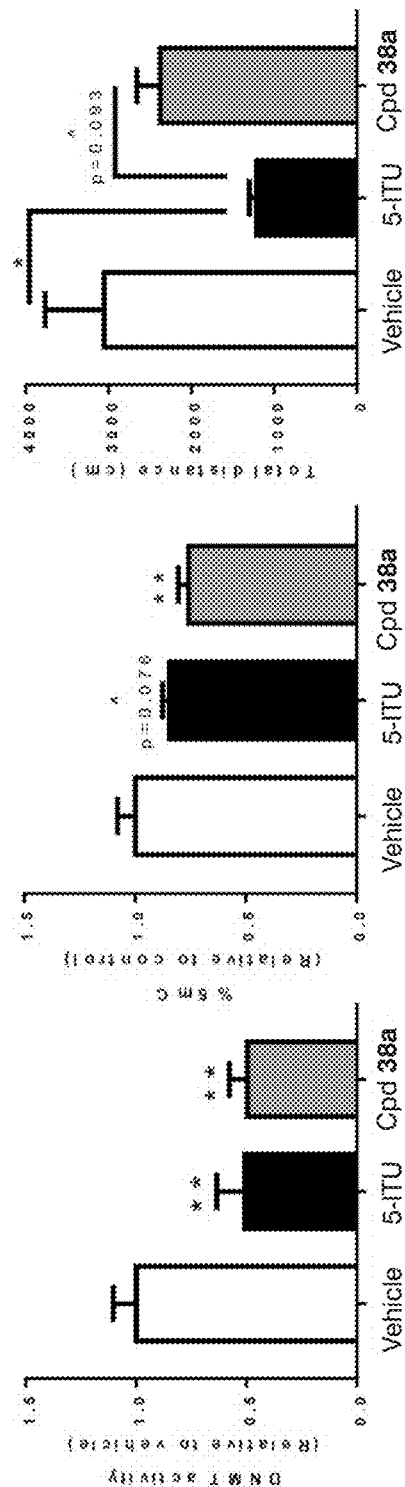
FIGS. 13A-13C: Plots showing relative DNMT activity (FIG. 13A), DNA methylation levels (FIG. 13B), and distance moved (FIG. 13C) when compound 38a and 5-ITU are injected into mice compared to a vehicle.

As shown in FIG. 13A, DNMT activity was significantly reduced in brain nuclear protein extracts from 5-ITU (p=0.0025) and compound 38a (p=0.0051) mice vs. vehicle treated mice (n=10-15).

As shown in FIG. 13B, Hippocampal DNA methylation levels were reduced with compound 38a (p=0.0084) and 5-ITU (p=0.076) vs. controls (n=8).

Figure 5:
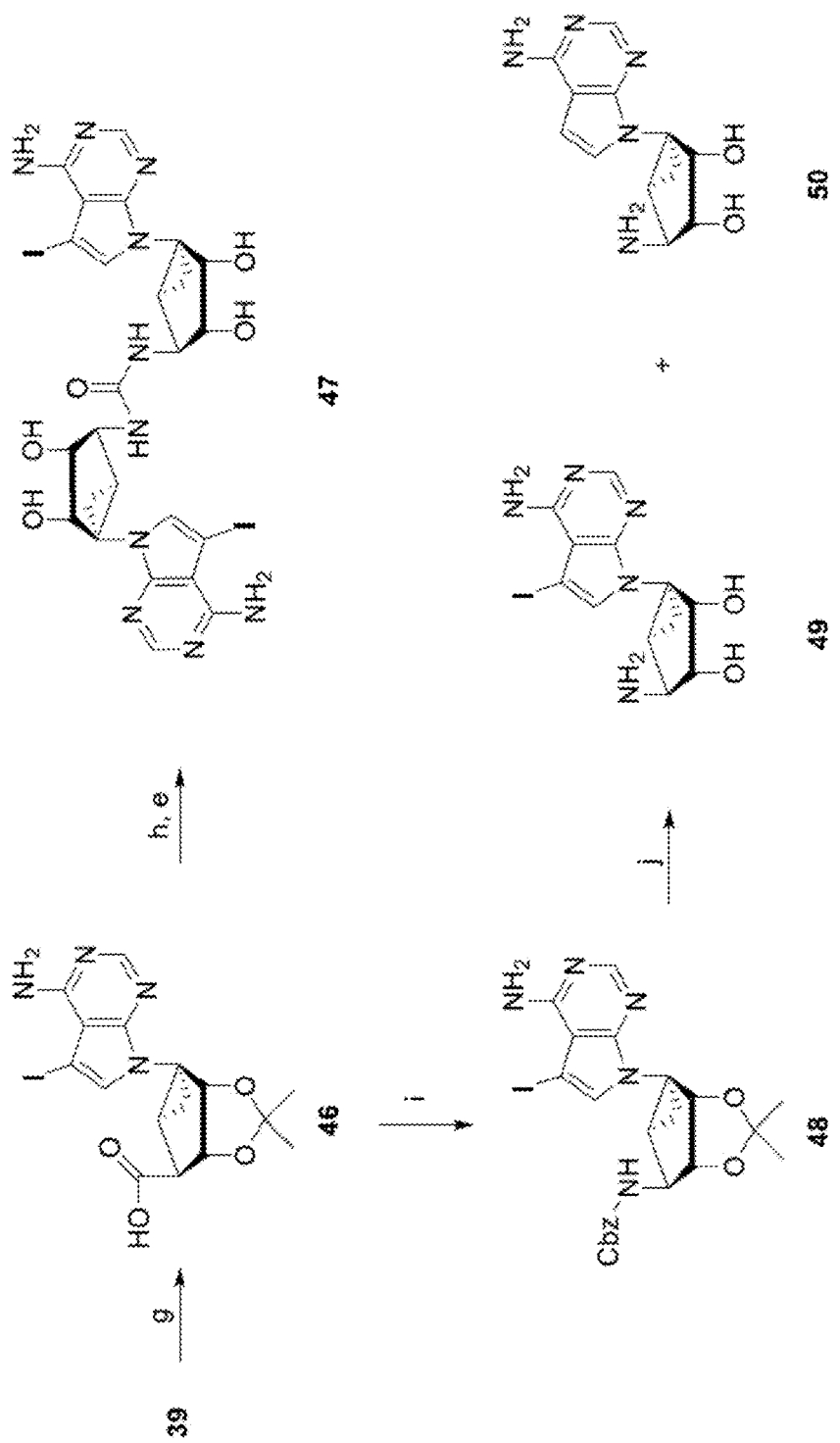
FIG. 5: A second portion of a synthetic scheme for the synthesis of 4'-position modified (S)-methanocarba analogues of 5-iodotubercidin. Reagents and conditions: (f) (i) anhydrous THF, PPh$_3$, rt, 18 h (ii) 25% NH$_4$OH (aq), 65° C., 4 h, 80%; (g) 4:1 CH$_3$CN—H$_2$O, BAIB, TEMPO, rt, 18 h, 49%; (h) DPPA, TEA, anhydrous t-BuOH, rt, 30 min, 90° C., 2 h; (i) (i) DPPA, TEA, anhydrous THF, rt, 18 h; (ii) toluene, benzyl alcohol, 110° C., 5 h, 17%; (j) anhydrous CH$_2$Cl$_2$, 33% HBr—CH$_3$COOH, 0° C.→rt, 2.5 h, 17%.

Side effects were indexed by mouse activity in an open field for 20 minutes following a single i.p. injection of vehicle, 5-ITU or compound 38a. As shown in FIG. 13C, 5-ITU decreased distance moved vs. vehicles (p=0.0324) and compound 38a (p=0.093) treated mice (n=4). Data are presented as the mean±SEM and analyzed by one-way ANOVA then uncorrected Fisher's LSD test with all comparisons relative to vehicle or Kruskal-Wallis then Dunn's multiple comparisons.

When injected systemically into mice, compound 38A (3.1 mg/kg i.p. tid) reduced DNMT activity and DNA methylation in the brain (FIGS. 9-11), showing that ADK-L activity of compound 38A in vitro associates with reduced DNA methylation in vivo. Importantly, DNMT activity was analyzed 1 h after the 3rd drug injection, suggesting that compound 38A administered systemically can affect DNA methylation in the brain. Compound 38A was not associated with any overt signs of sedation, whereas an epigenetically active dose of 5-ITU had major sedative side effects that immobilized the test subjects (FIG. 13C). These data demonstrate that compound 38A exerts epigenetic activity in the brain; however, free of side effects associated with the mixed ADK-L/ADK-S inhibitor 5-ITU.

Summary and Safety Considerations.

As determined in our primary assay compound 38A has an IC50 value for ADK<100 nM which is superior to 5-ITU. As determined in our secondary assay compound 38A reduces DNA methylation specifically in ADK-L cells without any off-target effects in ADK-Null or ADK-S cells. As deter-mined in our tertiary assay a systemic dose of compound 38A (3.1 mg/kg, i.p. tid) is bioactive in the brain and reduces DNA methylation in the hippocampus.

In addition, the following arguments support general safety of the proposed therapeutic methods:

(i) ADO occurs in all cells of the body and excessive levels are subject to endogenous metabolic clearance. The safety of intrathecal ADO has been demonstrated: no side effects were observed in dogs with intrathecal ADO at 7.2 mg/d for 26 d. Phase I clinical safety studies in volunteers with neuropathic pain demonstrated general safety of intrathecal ADO administration in concentrations of up to 2 mg. Since our goal is to target pathologically overexpressed ADK in TLE and to reinstate normal cellular ADO metabolism, we do not expect to induce an increase in ADO to supra-physilogical levels.

(ii) A goal is to target ADK-L, which primarily controls the nuclear (epigenetic) effects of ADO. Targeting ADK-L (as opposed to ADK-S) avoids the generation of excessive extracellular ADO, which in the past has been associated with adverse events.

(iii) By targeting ADK-L we may correct a specific maladaptive response of the epileptogenic brain, i.e. DNA hypermethylation caused by pathological over-expression of ADK. By targeting this maladaptive response specifically, we may limit adverse effects in healthy tissue and organs.

(iv) Limiting therapy to a restricted time frame of, for example, 1-4 weeks may likewise limit adverse effects (e.g. on liver) associated with long-term dosing.

(v) In genetic models, ADK-S and associated changes in extracellular ADO are the key driver for adenosine receptor mediated beneficial and adverse events. Therefore, targeting ADK-L creates a unique opportunity to avoid effects mediated by extracellular ADO.

Illustrative Embodiments

The following series of paragraphs, some or all of which may be alphanumerically designated for clarity and efficiency, describe additional aspects and features of the adenosine kinase inhibitors of the present disclosure. Each of these paragraphs can be combined with one or more other paragraphs, and/or with disclosure from elsewhere in this application, including the Appendices, in any suitable manner. Some of the paragraphs below expressly refer to and further limit other paragraphs, providing without limitation examples of some of the suitable combinations.

A1. An adenosine kinase inhibitor having the formula:

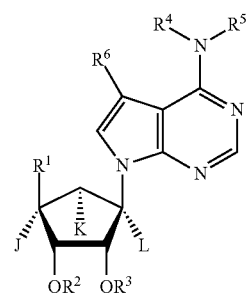

wherein J and K, considered in combination, are —$CH_2$—, or K and L, considered in combination, are —$CH_2$—;

$R^1$ is —$NH_2$, $C_1$-$C_6$ alkyl, $C_1$-$C_6$ alkoxy, or $C_1$-$C_6$ hydroxyalkyl;

$R^2$ and $R^3$ are independently $C_1$-$C_6$ alkyl;

$R^4$ is hydrogen, or $C_1$-$C_6$ alkyl; and $R^5$ and $R^6$ are independently aryl that is optionally further substituted by $C_1$-$C_6$ alkyl, hydroxy, $C_1$-$C_6$ alkoxy, or $NO_2$.

A2. The adenosine kinase inhibitor of paragraph A1, having the formula:

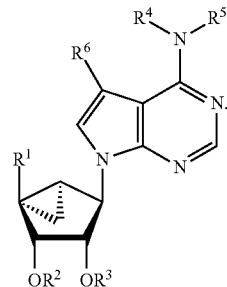

A3. The adenosine kinase inhibitor of paragraph A1, having the formula:

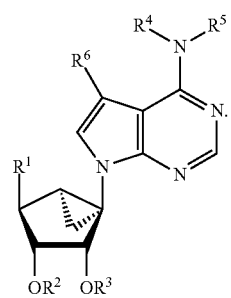

A4. The adenosine kinase inhibitor of paragraph A1, wherein $R^1$ is methyl or hydroxymethyl, $R^2$ and $R^3$ are independently hydrogen or methyl; $R^4$ is hydrogen; and each of $R^5$ and $R^6$ is phenyl or substituted phenyl.

A5. The adenosine kinase inhibitor of paragraph A1, wherein each of $R^5$ and $R^6$ is phenyl or phenyl substituted by fluorine.

A6. The adenosine kinase inhibitor of paragraph A1, having the formula:

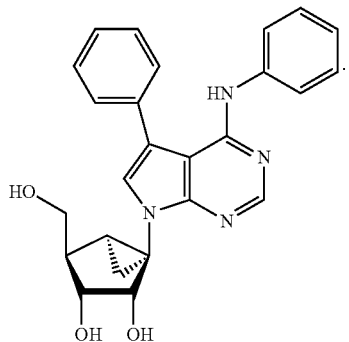

A7. The adenosine kinase inhibitor of paragraph A1, having the formula:

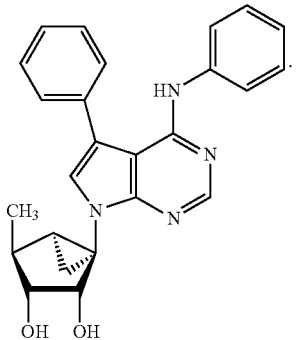

A8. The adenosine kinase inhibitor of paragraph A1, having the formula:

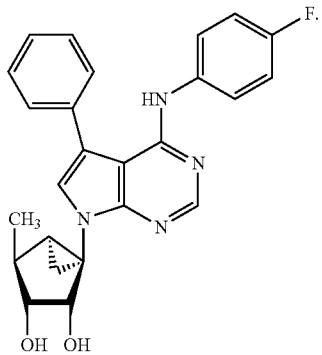

A9. The adenosine kinase inhibitor of paragraph A1, having the formula:

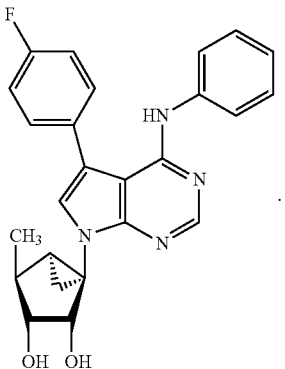

A10. The adenosine kinase inhibitor of paragraph A1, having the formula:

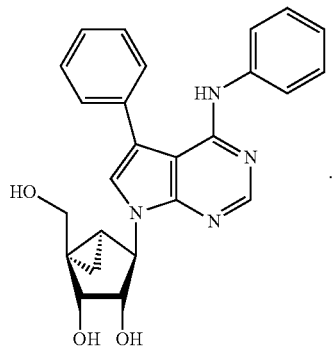

B1. A pharmaceutical composition, comprising an adenosine kinase inhibitor having the formula:

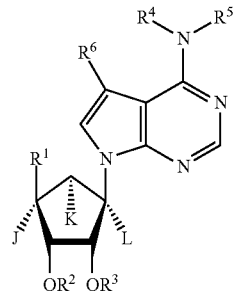

wherein J and K, considered in combination, are —$CH_2$—, or K and L, considered in combination, are —$CH_2$—;

$R^1$ is —$NH_2$, $C_1$-$C_6$ alkyl, $C_1$-$C_6$ alkoxy, or $C_1$-$C_6$ hydroxyalkyl;

$R^2$ and $R^3$ are independently $C_1$-$C_6$ alkyl;

$R^4$ is hydrogen, or $C_1$-$C_6$ alkyl; and $R^5$ and $R^6$ are independently aryl that is optionally further substituted by $C_1$-$C_6$ alkyl, hydroxy, $C_1$-$C_6$ alkoxy, or $NO_2$.

B2. The pharmaceutical composition of paragraph B1, further comprising one or more pharmaceutically acceptable carriers, excipients, preservatives, and/or diluents.

C1. A method of inhibiting seizures in a patient, comprising: administering an effective amount of an adenosine kinase inhibitor having the formula

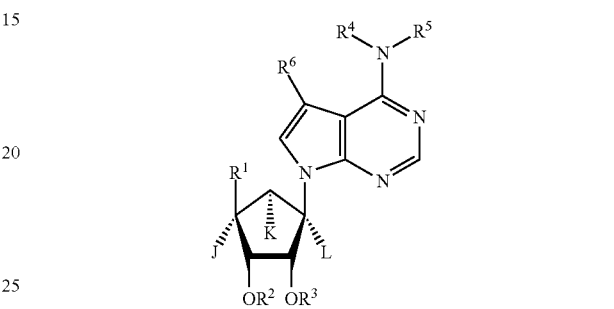

wherein J and K, considered in combination, are —$CH_2$—, or K and L, considered in combination, are —$CH_2$—;

$R^1$ is —$NH_2$, $C_1$-$C_6$ alkyl, $C_1$-$C_6$ alkoxy, or $C_1$-$C_6$ hydroxyalkyl;

$R^2$ and $R^3$ are independently $C_1$-$C_6$ alkyl;

$R^4$ is hydrogen, or $C_1$-$C_6$ alkyl; and $R^5$ and $R^6$ are independently aryl that is optionally further substituted by $C_1$-$C_6$ alkyl, hydroxy, $C_1$-$C_6$ alkoxy, or $NO_2$.

C2. The method of paragraph C1, wherein administering the adenosine kinase inhibitor includes administering the adenosine kinase inhibitor intravenously, orally, transdermally, subcutaneously, mucosally, intramuscularly, intranasally, intrapulmonary, parenterally, intrarectally or topically.

Although the present invention has been shown and described with reference to the foregoing operational principles and preferred embodiments, it will be apparent to those skilled in the art that various changes in form and detail may be made without departing from the spirit and scope of the invention. The present invention is intended to embrace all such alternatives, modifications and variances that fall within the scope of the appended claims.

It is believed that the disclosure set forth above encompasses multiple distinct embodiments with independent utility. While each of these embodiments has been disclosed in its preferred form, the specific aspects as disclosed and illustrated herein are not to be considered in a limiting sense as numerous variations are possible. The subject matter of the inventions includes all novel and non-obvious combinations and subcombinations of the various elements, features, functions and/or properties disclosed herein. Similarly, where the claims recite "a" or "a first" element or the equivalent thereof, such claims should be understood to include incorporation of one or more such elements, neither requiring nor excluding two or more such elements.

Various combinations and subcombinations of features, functions, elements, and/or properties may be claimed through presentation of new claims in a related application. Such new claims, whether they are directed to a different invention or directed to the same invention, whether different, broader, narrower or equal in scope to the original claims, are also regarded as included within the subject matter of the present disclosure.

What is claimed is:

1. An adenosine kinase inhibitor having the formula:

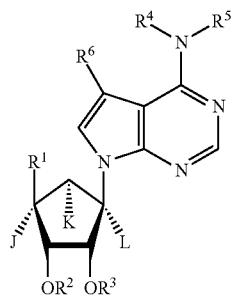

wherein J and K, considered in combination, are —CH$_2$—, or K and L, considered in combination, are —CH$_2$—;
R$^1$ is —NH$_2$, C$_1$-C$_6$ alkyl, C$_1$-C$_6$ alkoxy, or C$_1$-C$_6$ hydroxyalkyl;
R$^2$ and R$^3$ are independently C$_1$-C$_6$ alkyl;
R$^4$ is hydrogen, or C$_1$-C$_6$ alkyl; and
R$^5$ and R$^6$ are independently C$_6$-C$_{12}$ aryl, C$_3$-C$_8$ cycloalkyl, or C$_3$-C$_8$ heteroaryl, that is optionally further substituted.

2. The adenosine kinase inhibitor of claim 1, having the formula:

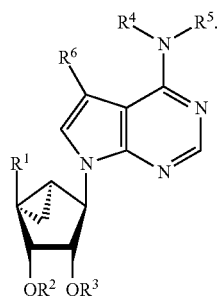

3. The adenosine kinase inhibitor of claim 1, having the formula:

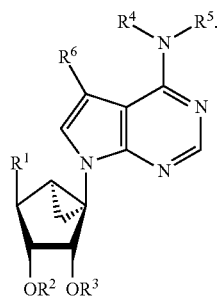

4. The adenosine kinase inhibitor of claim 1, wherein R$^1$ is methyl or hydroxymethyl, R$^2$ and R$^3$ are independently hydrogen or methyl; R$^4$ is hydrogen; and each of R$^5$ and R$^6$ is phenyl or substituted phenyl.

5. The adenosine kinase inhibitor of claim 1, wherein where R$^5$ or R$^6$ is an aryl substituent, the aryl substituent is optionally and independently further substituted one or more times by halogen, C$_1$-C$_6$ haloalkyl, C$_1$-C$_6$ hydroxyalkyl, C$_1$-C$_6$ alkoxy, sulfonyloxy, carboxyalkyl, nitro, C$_1$-C$_6$ sulfonyloxyalkyl, or arylcarbonyl.

6. The adenosine kinase inhibitor of claim 1, wherein where R$^5$ or R$^6$ is a cycloalkyl, the cycloalkyl substituent is optionally and independently further substituted one or more times by halogen, C$_1$-C$_6$ haloalkyl, C$_1$-C$_6$ hydroxyalkyl, C$_1$-C$_6$ alkoxy, sulfonyloxy, carboxyalkyl, C$_1$-C$_6$ sulfonyloxyalkyl, or arylcarbonyl.

7. The adenosine kinase inhibitor of claim 1, wherein where R$^5$ or R$^6$ is a heteroaryl substituent, the heteroaryl substituent is optionally and independently further substituted one or more times by halogen, C$_1$-C$_6$ haloalkyl, amino, nitro, C$_1$-C$_6$ alkyl, C$_6$ hydroxyalkyl, C$_1$-C$_6$ alkoxy, aryl, hydroxyl, carboxyl, sulfonyloxy, carboxyalkyl, C$_1$-C$_6$ sulfonyloxyalkyl, sulfonamide, C$_1$-C$_6$ alkylcarbonyl, or arylcarbonyl.

8. The adenosine kinase inhibitor of claim 1, wherein R$^5$ and R$^6$ are each independently aryl that is optionally further substituted by halogen, C$_1$-C$_6$ alkyl, C$_1$-C$_6$ perfluoroalkyl, hydroxy, C$_1$-C$_6$ alkoxy, or NO$_2$.

9. The adenosine kinase inhibitor of claim 1, wherein each of R$^5$ and R$^6$ is phenyl or phenyl substituted by fluorine.

10. The adenosine kinase inhibitor of claim 1, having the formula:

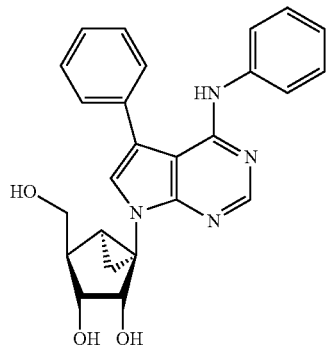

11. The adenosine kinase inhibitor of claim 1, having the formula:

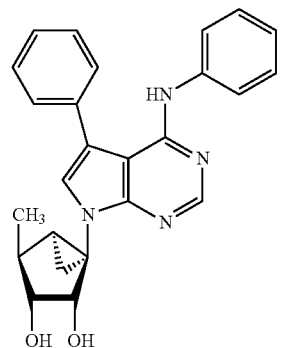

12. The adenosine kinase inhibitor of claim 1, having the formula:

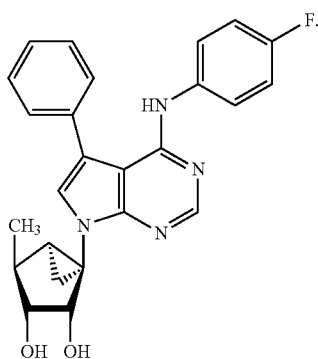

13. The adenosine kinase inhibitor of claim 1, having the formula:

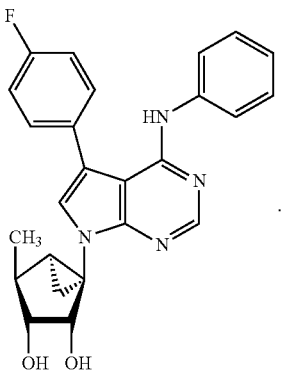

14. The adenosine kinase inhibitor of claim 1, having the formula:

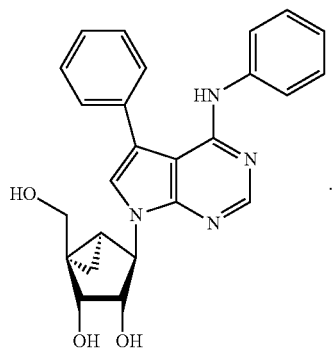

15. A pharmaceutical composition, comprising an adenosine kinase inhibitor having the formula:

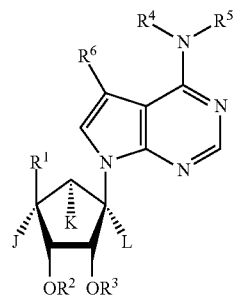

wherein J and K, considered in combination, are —CH$_2$—, or K and L, considered in combination, are —CH$_2$—;
$R^1$ is —NH$_2$, C$_1$-C$_6$ alkyl, C$_1$-C$_6$ alkoxy, or C$_1$-C$_6$ hydroxyalkyl;
$R^2$ and $R^3$ are independently C$_1$-C$_6$ alkyl;
$R^4$ is hydrogen, or C$_1$-C$_6$ alkyl; and
$R^5$ and $R^6$ moieties are independently C$_6$-C$_{12}$ aryl, C$_3$-C$_8$ cycloalkyl, or C$_3$-C$_8$ heteroaryl, that is optionally further substituted.

16. The pharmaceutical composition of claim 15, wherein $R^1$ is methyl or hydroxymethyl, $R^2$ and $R^3$ are independently hydrogen or methyl; $R^4$ is hydrogen; and each of $R^5$ and $R^6$ is independently aryl that is optionally further substituted by halogen, C$_1$-C$_6$ alkyl, hydroxy, C$_1$-C$_6$ alkoxy, or NO$_2$.

17. The pharmaceutical composition of claim 15, wherein where $R^5$ or $R^6$ is an aryl substituent, the aryl substituent is optionally and independently further substituted one or more times by halogen, C$_1$-C$_6$ haloalkyl, C$_1$-C$_6$ hydroxyalkyl, C$_1$-C$_6$ alkoxy, sulfonyloxy, carboxyalkyl, nitro, C$_1$-C$_6$ sulfonyloxyalkyl, or arylcarbonyl;
where $R^5$ or $R^6$ is a cycloalkyl, the cycloalkyl substituent is optionally and independently further substituted one or more times by halogen, C$_1$-C$_6$ haloalkyl, C$_1$-C$_6$ hydroxyalkyl, C$_1$-C$_6$ alkoxy, sulfonyloxy, carboxyalkyl, C$_1$-C$_6$ sulfonyloxyalkyl, or arylcarbonyl; and
where $R^5$ or $R^6$ is a heteroaryl substituent, the heteroaryl substituent is optionally and independently further substituted one or more times by halogen, C$_1$-C$_6$ haloalkyl, amino, nitro, C$_1$-C$_6$ alkyl, C$_1$-C$_6$ hydroxyalkyl, C$_1$-C$_6$ alkoxy, aryl, hydroxyl, carboxyl, sulfonyloxy, carboxyalkyl, C$_1$-C$_6$ sulfonyloxyalkyl, sulfonamide, C$_1$-C$_6$ alkylcarbonyl, or arylcarbonyl.

18. The pharmaceutical composition of claim 15, further comprising one or more pharmaceutically acceptable carriers, excipients, preservatives, and/or diluents.

19. A method for treating epilepsy, comprising:
administering an effective amount of an adenosine kinase inhibitor having the formula

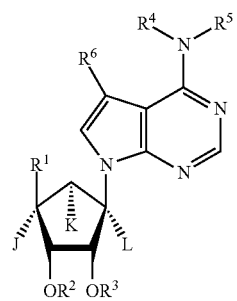

wherein J and K, considered in combination, are —CH$_2$—, or K and L, considered in combination, are —CH$_2$—;
$R^1$ is —NH$_2$, C$_1$-C$_6$ alkyl, C$_1$-C$_6$ alkoxy, or C$_1$-C$_6$ hydroxyalkyl;
$R^2$ and $R^3$ are independently C$_1$-C$_6$ alkyl;
$R^4$ is hydrogen, or C$_1$-C$_6$ alkyl; and
$R^5$ and $R^6$ are independently C$_6$-C$_{12}$ aryl, C$_3$-C$_8$ cycloalkyl, or C$_3$-C$_8$ heteroaryl, that is optionally further substituted.

20. The method of claim 19, wherein administering the adenosine kinase inhibitor includes administering the adenosine kinase inhibitor intravenously, orally, transdermally, subcutaneously, mucosally, intramuscularly, intranasally, intrapulmonary, parenterally, intrarectally, or topically.

21. The method of claim 19, wherein treating epilepsy and its progression in a patient includes inhibiting seizures in the patient.

\* \* \* \* \*